(12) United States Patent
Ohad et al.

(10) Patent No.: US 10,839,964 B2
(45) Date of Patent: Nov. 17, 2020

(54) CLOUD-BASED CLINICAL INFORMATION SYSTEMS AND METHODS OF USE

(71) Applicant: General Electric Company, Schenectady, NY (US)

(72) Inventors: Nimrod Ohad, Barrington, IL (US); Mark Alan Cole, South Burlington, VT (US); Mike Lowell Sharland, Barrington, IL (US); Ronen Gans, Park Ridge, NJ (US); Patrick Leo Hughes, Barrington, IL (US); Todd McNitt, Barrington, IL (US)

(73) Assignee: General Electric Company, Schenectady, NY (US)

( * ) Notice: Subject to any disclaimer, the term of this patent is extended or adjusted under 35 U.S.C. 154(b) by 258 days.

(21) Appl. No.: 15/966,988

(22) Filed: Apr. 30, 2018

(65) Prior Publication Data

US 2018/0254094 A1 Sep. 6, 2018

Related U.S. Application Data

(63) Continuation of application No. 14/188,354, filed on Feb. 24, 2014, now Pat. No. 9,959,386.

(Continued)

(51) Int. Cl.
*G16H 70/00* (2018.01)
*G06F 19/00* (2018.01)
(Continued)

(52) U.S. Cl.
CPC .............. *G16H 70/00* (2018.01); *G06F 19/00* (2013.01); *G06F 19/324* (2013.01); *G06Q 50/24* (2013.01);
(Continued)

(58) Field of Classification Search
CPC ................................................ G06Q 50/22–24
See application file for complete search history.

(56) References Cited

U.S. PATENT DOCUMENTS

2004/0039757 A1 2/2004 McClure
2009/0276463 A1* 11/2009 Miller .................... G16H 10/20
(Continued)

OTHER PUBLICATIONS

United States Patent and Trademark Office, "Notice of Allowance," issued in connection with U.S. Appl. No. 14/188,354, dated Dec. 26, 2017, 10 pages.

(Continued)

*Primary Examiner* — Robert A Sorey
(74) *Attorney, Agent, or Firm* — Hanley, Flight and Zimmerman, LLC

(57) ABSTRACT

An example method includes monitoring healthcare information employed by a local information system of a first healthcare entity via an edge device located at a facility of the first healthcare entity and in communication with a local information system. The edge device is to implement a local cloud system. The local cloud system is to be accessible by only the first healthcare entity and healthcare entities affiliated with the first healthcare entity. The example method also includes determining if the healthcare information has a first characteristic via the edge device, determining if the healthcare information has a second characteristic via the edge device, and automatically uploading the healthcare information onto the local cloud system if the healthcare information has the first characteristic. The example method also includes automatically uploading the healthcare information onto a remote cloud system if the healthcare information has the second characteristic.

22 Claims, 23 Drawing Sheets

Related U.S. Application Data

(60) Provisional application No. 61/909,957, filed on Nov. 27, 2013.

(51) Int. Cl.

| | | |
|---|---|---|
| *G16H 70/60* | (2018.01) | |
| *H04L 29/08* | (2006.01) | |
| *G06Q 50/24* | (2012.01) | |
| *G16H 10/60* | (2018.01) | |
| *G16H 80/00* | (2018.01) | |
| *G16H 40/20* | (2018.01) | |

(52) U.S. Cl.
CPC .............. *G16H 10/60* (2018.01); *G16H 40/20* (2018.01); *G16H 70/60* (2018.01); *G16H 80/00* (2018.01); *H04L 67/1002* (2013.01); *H04L 67/12* (2013.01)

(56) References Cited

U.S. PATENT DOCUMENTS

| | | |
|---|---|---|
| 2011/0022812 A1 | 1/2011 | van der Linden et al. |
| 2012/0130781 A1 | 5/2012 | Li |
| 2012/0203094 A1 | 8/2012 | Suri |
| 2012/0303814 A1 | 11/2012 | Ferris |
| 2013/0005374 A1 | 1/2013 | Uusitalo |
| 2013/0097127 A1 | 4/2013 | Mohapatra et al. |
| 2013/0132109 A1 | 5/2013 | Mruthyunjaya et al. |
| 2013/0176988 A1 | 7/2013 | Wang et al. |
| 2013/0179192 A1* | 7/2013 | Rajendran ............. G06F 19/321 705/3 |
| 2013/0208966 A1 | 8/2013 | Zhao et al. |
| 2013/0227670 A1 | 8/2013 | Ahmad et al. |
| 2014/0026194 A1 | 1/2014 | Smith |
| 2014/0067758 A1 | 3/2014 | Boldyrev et al. |
| 2014/0114672 A1 | 4/2014 | Wright et al. |
| 2014/0223507 A1 | 8/2014 | Xu |
| 2014/0324457 A1 | 10/2014 | Kim et al. |
| 2014/0372149 A1 | 12/2014 | Friese et al. |
| 2015/0149196 A1 | 5/2015 | Ohad et al. |

OTHER PUBLICATIONS

United States Patent and Trademark Office, "Non-Final Office action," issued in connection with U.S. Appl. No. 14/188,354, dated Jul. 7, 2017, 35 pages.

United States Patent and Trademark Office, "Advisory Action," issued in connection with U.S. Appl. No. 14/188,354, dated Jul. 5, 2016, 5 pages.

United States Patent and Trademark Office, "Final Office action," issued in connection with U.S. Appl. No. 14/188,354, dated Apr. 18, 2016, 34 pages.

United States Patent and Trademark Office, "Non-Final Office action," issued in connection with U.S. Appl. No. 14/188,354, dated Oct. 7, 2015, 33 pages.

\* cited by examiner

Inbox | Contacts & Directories | Activities & Reports | Admin

Received Cases | Shared Cases | Cases by Type | Drafts | All Cases — 1101

1100

Inbox

Dr Mike sharland  → ☆
10/14/13 17:14
Smith .Ohn
Multi-Discipline Tumor Board
Please take a look at this unique study
📎 1 💬 0

Dr Mike sharland  → ☆
10/14/13 21:55
Zimmer 1
Second Opinion
Please review this study
📎 1 💬 0

← ↑ ↓ Reject | Add case | Add to DICOM

Smith John
S120050-LT
Sex   Age   DOB   PCP

Case Summary  ∨

1102

History (You) Mike.Sharland @med.ge.com   To: Shradha.Pathak@ge.com   10/14/13 17:44
Clinical Reason Multi-Discipline Tumor Board   10/14/13 17:44
Please take a look at this unique study (You) Mike.Sha1and @med.ge.com   To: kshibj.gajjar@citiustech.com 10/05/13 16:49
Clinical Reason second Opinion Create a case

FIG. 11

CLOUD-BASED CLINICAL INFORMATION SYSTEMS AND METHODS OF USE

RELATED APPLICATIONS

This patent claims the benefit of U.S. patent application Ser. No. 14/188,354, filed on Feb. 24, 2014, entitled "CLOUD-BASED CLINICAL INFORMATION SYSTEMS AND METHODS OF USE," which claims priority to U.S. Provisional Patent Application Ser. No. 61/909,957, filed Nov. 27, 2013, entitled "Cloud-Based Clinical Information Systems and Methods of Use," both of which are hereby incorporated herein by reference in their entireties.

FEDERALLY SPONSORED RESEARCH OR DEVELOPMENT

[Not Applicable]

MICROFICHE/COPYRIGHT REFERENCE

[Not Applicable]

BACKGROUND

Healthcare entities such as hospitals, clinics, or clinical groups often employ local information systems to store and manage patient information. If a first healthcare entity having a first local information system refers a patient to a second healthcare entity having a second local information system, personnel at the first healthcare entity typically manually retrieves patient information from the first information system and stores the patient information on a storage device such as a compact disk (CD). The personnel then transport the storage device to the second healthcare entity, which employs personnel to upload the patient information from the storage device onto the second information system.

BRIEF SUMMARY

Cloud-based clinical information systems and methods of use are disclosed herein.

Certain examples provide a hybrid cloud system including a remote cloud system to be accessible via a public network by a plurality of unaffiliated healthcare entities. The example hybrid cloud system also includes an edge device to implement a local cloud system to be accessible only via a private network by a first healthcare entity of the plurality of healthcare entities and a second healthcare entity affiliated with the first healthcare entity. The edge device is to be located at a facility associated with the first healthcare entity and in communication with the remote cloud system and a local healthcare information system of the first healthcare entity. The edge device is to monitor healthcare information employed by the local healthcare information system and determine if the healthcare information has a first characteristic and a second characteristic. If the healthcare information has the first characteristic, the edge device is to upload a first portion of the healthcare information onto the remote cloud system. The example edge device is to upload a second portion of the healthcare information onto the local cloud system if the healthcare information has the second characteristic. The remote cloud system is to employ the first portion of the healthcare information based on the first characteristic, and the local cloud system is to employ the second portion of the healthcare information based on the second characteristic.

Certain examples provide a method to manage information flow between a local information system, a local cloud system and a remote cloud system employed by a first healthcare entity. The example method includes monitoring healthcare information employed by the local information system of the first healthcare entity via an edge device located at a facility of the first healthcare entity and in communication with the local information system. The edge device is to be implemented by the local cloud system. The local cloud system is to be accessible by only the first healthcare entity and healthcare entities affiliated with the first healthcare entity. The example method also includes determining if the healthcare information has a first characteristic via the edge device, determining if the healthcare information has a second characteristic via the edge device, and automatically uploading the healthcare information onto the local cloud system if the healthcare information has the first characteristic. The example method also includes automatically uploading the healthcare information onto the remote cloud system if the healthcare information has the second characteristic. The remote cloud system is to be accessible by the first healthcare entity via the edge device and by healthcare entities not affiliated with the first healthcare entity via a web application.

Certain examples provide a tangible, computer readable storage medium including instructions which, when executed, implement a method to manage information flow between a local information system, a local cloud system and a remote cloud system employed by a first healthcare entity. The example method includes monitoring healthcare information communicated between the first healthcare entity and a second healthcare entity via the local cloud system. The second healthcare entity is to be affiliated with the first healthcare entity, and the local cloud system is to be accessible by the first healthcare entity and the second healthcare entity via a private network. The example method also includes determining if the healthcare information has a first characteristic via an edge device located at a facility associated with the first healthcare entity. The edge device is to implement the local cloud system and be in communication with the local information system and the remote cloud system. The remote cloud system is to be accessible by a plurality of healthcare entities unaffiliated with the first healthcare entity via a public network. The example method further includes automatically uploading the healthcare information onto the remote cloud system via the edge device if the healthcare information has the first characteristic.

BRIEF DESCRIPTION OF SEVERAL VIEWS OF THE DRAWINGS

FIG. 11 illustrates another example user interface disclosed herein.

Figure 1:
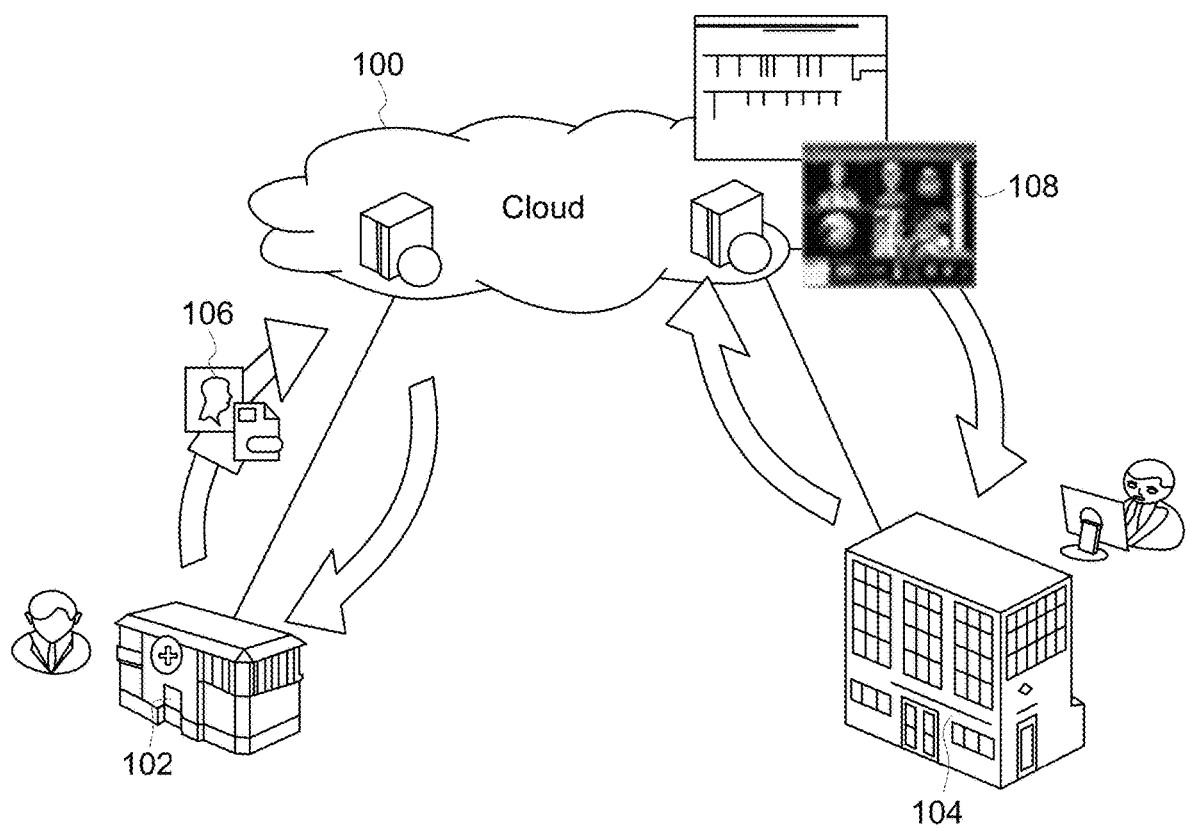
FIG. 1 is illustrates an example cloud-based clinical information system employed by a first healthcare entity to share information with a second healthcare entity.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

Cloud-based clinical information systems and methods of use are disclosed herein. An example cloud-based clinical information system described herein enables healthcare entities (e.g., patients, clinicians, sites, groups, communities, and/or other entities) to share information via web-based applications, cloud storage and cloud services. For example, the cloud-based clinical information system may enable a first clinician to securely upload information into the cloud-based clinical information system to allow a second clinician to view and/or download the information via a web application. Thus, for example, the first clinician may upload an x-ray image into the cloud-based clinical information system, and the second clinician may view the x-ray image via a web browser and/or download the x-ray image onto a local information system employed by the second clinician.

In some examples, a first healthcare entity may register with the cloud-based clinical information system to acquire credentials and/or access the cloud-based clinical information system. To share information with a second healthcare entity and/or gain other enrollment privileges (e.g., access to local information systems), the first healthcare entity enrolls with the second healthcare entity. In some examples, the example cloud-based clinical information system segregates registration from enrollment. For example, a clinician may be registered with the cloud-based clinical information system and enrolled with a first hospital and a second hospital. If the clinician no longer chooses to be enrolled with the second hospital, enrollment of the clinician with the second hospital can be removed or revoked without the clinician losing access to the cloud-based clinical information system and/or enrollment privileges established between the clinician and the first hospital.

In some examples, business agreements between healthcare entities are initiated and/or managed via the cloud-based clinical information system. For example, if the first healthcare entity is unaffiliated with the second healthcare entity (e.g., no legal or business agreement exists between the first healthcare entity and the second healthcare entity) when the first healthcare entity enrolls with the second healthcare entity, the cloud-based clinical information system provides the first healthcare entity with a business agreement and/or terms of use that the first healthcare entity executes prior to being enrolled with the second healthcare entity. The business agreement and/or the terms of use may be generated by the second healthcare entity and stored in the cloud-based clinical information system. In some examples, based on the agreement and/or the terms of use, the cloud-based clinical information system generates rules that govern what information the first healthcare entity may access from the second healthcare entity and/or how information from the second healthcare entity may be shared by the first healthcare entity with other entities and/or other rules.

In some examples, the cloud-based clinical information system may employ a hierarchal organizational scheme based on entity types to facilitate referral network growth, business agreement management, and regulatory and privacy compliance. Example entity types include patients, clinicians, groups, sites, integrated delivery networks, communities and/or other entity types. A user, which may be a healthcare entity or an administrator of a healthcare entity, may register as a given entity type within the hierarchal organizational scheme to be provided with predetermined rights and/or restrictions related to sending information and/or receiving information via the cloud-based clinical information system. For example, a user registered as a patient may receive or share any patient information of the user while being prevented from accessing any other patients' information. In some examples, a user may be registered as two types of healthcare entities. For example, a healthcare professional may be registered as a patient and a clinician.

In some examples, the cloud-based clinical information system includes an edge device located at healthcare facility (e.g., a hospital). The edge device may communicate with a protocol employed by the local information system(s) to function as a gateway or mediator between the local information system(s) and the cloud-based clinical information system. In some examples, the edge device is used to automatically generate patient and/or exam records in the local information system(s) and attach patient information to the patient and/or exam records when patient information is sent to a healthcare entity associated with the healthcare facility via the cloud-based clinical information system.

In some examples, the cloud-based clinical information system generates user interfaces that enable users to interact with the cloud-based clinical information system and/or communicate with other users employing the cloud-based clinical information system. An example user interface described herein enables a user to generate messages, receive messages, create cases (e.g., patient orders), share information, receive information, view information, and/or perform other actions via the cloud-based clinical information system.

FIG. 1 illustrates an example cloud-based clinical information system 100 disclosed herein. In the illustrated example, the cloud-based clinical information system 100 is employed by a first healthcare entity 102 and a second healthcare entity 104. As described in greater detail below, example entity types include a community, an integrated delivery network (IDN), a site, a group, a clinician, and a patient and/or other entities.

In the illustrated example, the first healthcare entity 102 employs the example cloud-based clinical information system 100 to facilitate a patient referral. Although the following example is described in conjunction with a patient referral (e.g., a trauma transfer), the cloud-based information system 100 may be used to share information to acquire a second opinion, conduct a medical analysis (e.g., a specialist located in a first location may review and analyze a medical image captured at a second location), facilitate care of a patient that is treated in a plurality of medical facilities, and/or in other situations and/or for other purposes.

In the illustrated example, the first healthcare entity 102 may be a medical clinic that provides care to a patient. The first healthcare entity 102 generates patient information (e.g., contact information, medical reports, medical images, and/or any other type of patient information) associated with the patient and stores the patient information in a first local information system (e.g., PACS/RIS and/or any other local information system). To refer the patient to the second healthcare entity 104, the first healthcare entity posts or uploads an order 106, which includes relevant portions of the patient information, to the cloud-based clinical information system 100 and specifies that the patient is to be referred to the second healthcare entity. For example, the first healthcare entity 102 may use a user interface (FIGS. 9-11) generated via the cloud-based clinical information system 100 to upload the order 106 via the internet from the first local information system to the cloud-based clinical information system 100 and direct the cloud-based information system 100 notify the second healthcare entity 104 of the referral and/or enable the second healthcare entity 104 to access the order 106. In some examples, the cloud-based clinical information system 100 generates a message including a secure link to the order 106 and emails the message to the second healthcare entity 104. The second healthcare entity 104 may then view the order 106 through a web browser 108 via the cloud-based clinical information system 100, accept and/or reject the referral, and/or download the order 106 including the patient information into a second local information system (e.g., PACS/RIS) of the second healthcare entity 104. As described in greater detail below, the cloud-based-based clinical information system 100 manages business agreements between healthcare entities to enable unaffiliated healthcare entities to share information, thereby facilitating referral network growth.

Figure 2:
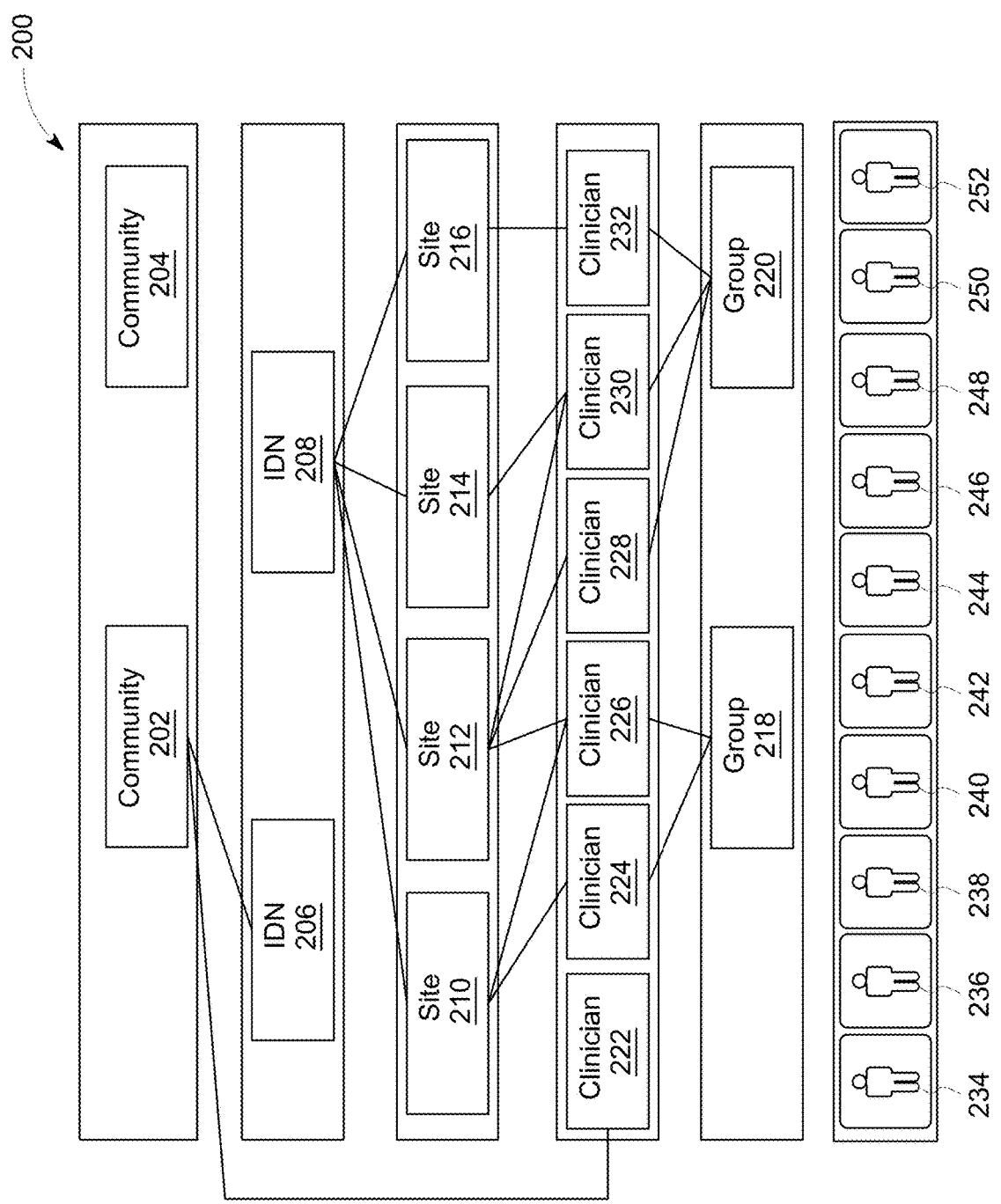
FIG. 2 is a block diagram illustrating an example hierarchal organizational system employed by the example cloud-based clinical information system of FIG. 1.

FIG. 2 illustrates an example hierarchal organization scheme 200 disclosed herein. In some examples, credentials are assigned and/or rules for accessing (e.g., viewing, receiving, downloading, etc.) information and/or sharing (e.g., uploading, sending, etc.) information via the cloud-based clinical information system 100 is governed and/or determined by the cloud-based information system 100 according to the hierarchal organization scheme 200. In the illustrated example, the hierarchal organizational scheme 200 is organized based on entity types. In the illustrated example, the entity types include communities 202, 204, IDNs 206, 208, sites 210, 212, 214, 216, groups 218, 220, clinicians 222, 224, 226, 228, 230, 232, 234, and patients 234, 236, 238, 240, 242, 244, 246, 248, 250, 252. Other examples include other entity types.

In some examples, the communities 202, 204 are legal entities. In some examples, the communities 202, 204 are defined by subject matter (e.g., medical practice type, research area and/or any other subject matter) and/or geographic location. For example, the community 202 may be a plurality of individuals, hospitals, research facilities, etc. cooperating to form a research collaboration.

The IDNs 206, 208 may be a plurality of facilities and/or providers that provide a continuum of care to a market or geographic area. For example, the IDN 206 may be a plurality of medical facilities having business and/or legal relationships.

The sites 210, 212, 214, 216 are medical facilities such as a hospitals, imaging centers and/or any other type of medical facility.

The groups 218, 220 are a plurality of individuals having a legal-based or interest-based relationship. For example, the group 218 may be a limited liability corporation, and the group 220 may be composed of a plurality of clinicians.

Clinicians 222, 224, 226, 228, 230, 232, 234 are healthcare professionals such as physicians, technicians, administrative professionals (e.g., file room clerks, scheduling administrators, reporting administrators, and/or any other administrative professionals), nurses, students, researchers, and/or any other healthcare professionals. In some examples, the clinicians 222, 224, 226, 228, 230, 232, 234 are employed by one or more of the sites 210, 212, 214, 216 and/or the groups 218, 220.

The patients 234, 236, 238, 240, 242, 244, 246, 248, 250, 252 are individuals who will be or have been under the care of one or more of the clinicians 222, 224, 226, 228, 230, 232, 234.

In the illustrated example, credentials and/or rules for accessing and sharing information via the cloud-based clinical information system 100 are assigned and/or governed based on the entity types. Example rules for accessing and sharing information via the cloud-based clinical information system 100 include rules related to regulatory compliance and privacy such as, for example, rules to comply with the Health Insurance Portability and Accountability Act (HIPAA). For example, one of the patients 234, 236, 238, 240, 242, 244, 246, 248, 250, 252 may access his/her patient information from any healthcare entity in communication with the cloud-based clinical information system 100 and share his/her patient information with any healthcare entity in communication with the cloud-based clinical information system 100. However, the cloud-based clinical information system 100 prohibits or prevents the patients 234, 236, 238, 240, 242, 244, 246, 248, 250, 252 from viewing, receiving or sharing other patients' information. In some examples, the cloud-based clinical information system 100 enables the clinicians 222, 224, 226, 228, 230, 232, 234 to view, receive and/or share information related to any of the patients 234, 236, 238, 240, 242, 244, 246, 248, 250, 252 which are under the clinicians' care. However, the cloud-based clinical information system 100 may prevent one of the clinicians 222, 224, 226, 228, 230, 232, 234 from viewing and/or sharing information related to one of the patients 234, 236, 238, 240, 242, 244, 246, 248, 250, 252 not under the clinicians' care.

In some examples, one healthcare entity is a member of one or more other healthcare entities. For example, as illustrated in FIG. 2, the clinician 232 is a member of the group 220 and the site 216. Thus, the clinician 232 may access and/or share information that is accessible to the group 220 and the site 216 and associated with the clinician 232 via the cloud-based clinical information system 100. For example, the clinician 232 may be employed by both the group 220 and the site 216, and the clinician 232 may use the cloud-based clinical information system 100 to access and/or share information related to patients under the care of the clinician 232 at either of the group 220 and the site 216 even if, for example, the group 220 and the site 216 are not affiliated with each other. As described in greater detail below, a first healthcare entity (e.g., the clinician 222) may become a member of second healthcare entity (e.g., IDN 206) by enrolling in the second healthcare entity via the cloud-based clinical information system.

Figure 3:
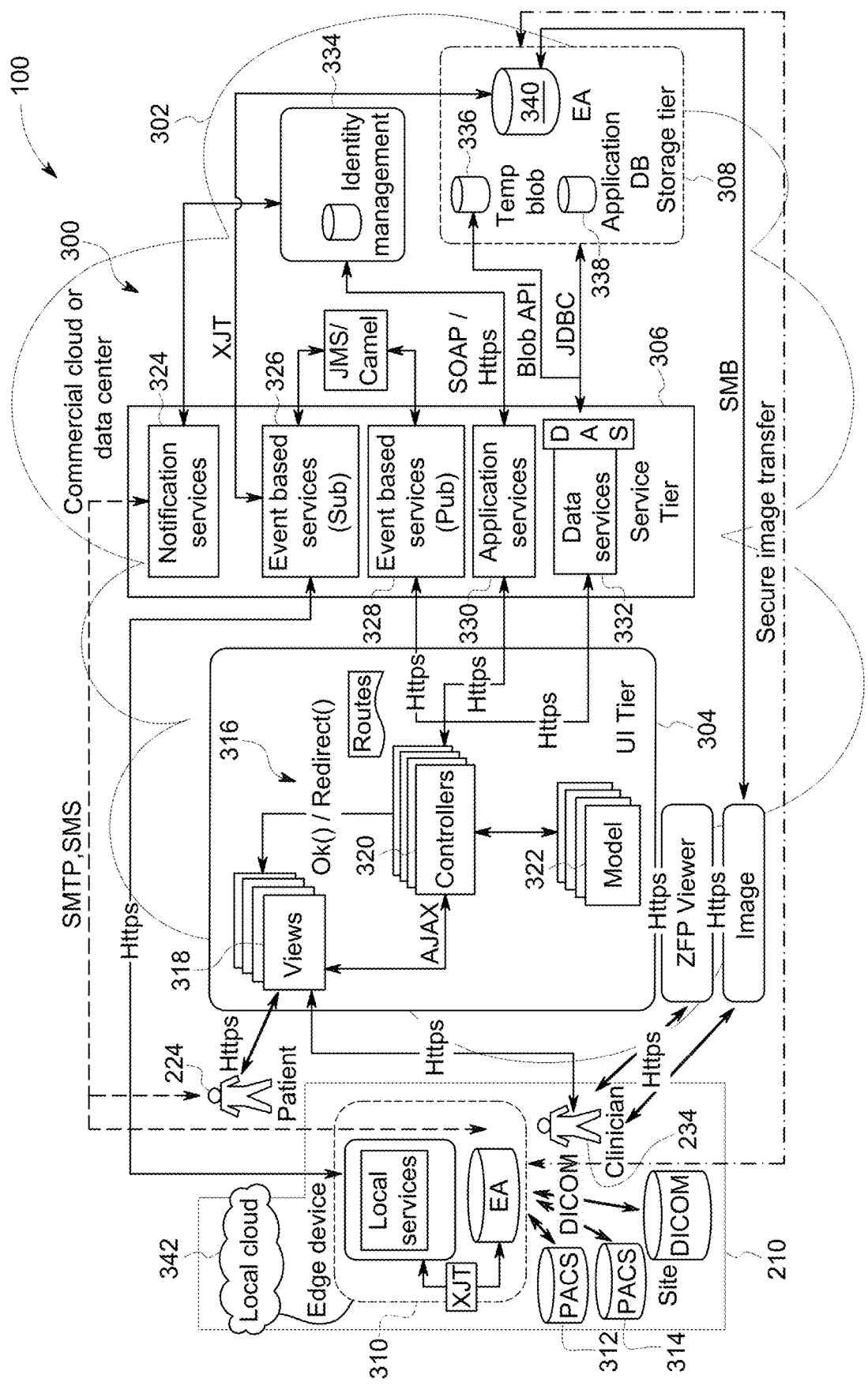
FIG. 3 illustrates an example architecture that may be used to implement the example cloud-based clinical information system of FIG. 1.

FIG. 3 illustrates example architecture 300 to implement the example cloud-based clinical information system 100 of FIG. 1. In the illustrated example, the cloud-based clinical information system 100 includes a remote cloud system 302 ("cloud," "remote cloud") having a web/user interface tier 304, a service tier 306 and a storage tier 308. In the illustrated example, the clinician 234 is located at the site 210. An example edge device 310 is located at the site 234 and facilitates communication between the remote cloud system 302 and local information systems 312, 314 employed by the site 210. For example, the edge device 310 may communicate via Digital Imaging and Communications in Medicine (DICOM) and/or Health Level Seven (HL7) protocols with the local information systems 312, 314 to generate patient and/or exam records in the local information systems 312, 314, retrieve information from the local information system 312, 314 and upload the information into the cloud 300, store information in the local information systems 312, 314, and/or perform other actions. In some examples, the local information systems 312, 314 include picture archiving and communication systems (PACS), electronic health records (EMR) systems, radiology information systems (RIS) and/or other types of local information systems.

In some examples, the web/user interface tier 304 implements a user interface generator to build a user experience. In some examples, the interface generator builds a user experience via model-view-controller architecture 316 including views 318, controllers 320 and models 322. For example, the views 318 request information from the models 322 to generate user interfaces that enable the clinician 234 and/or the patient 224 to view information stored in the remote cloud system 302 via the storage tier 308. In some examples, views 318 generate zero footprint viewers that enable the clinician 234 and/or the patient 224 to view information such as medical images using a web browser. In some examples, the views 318 generate user interfaces that enable the clinician 234 and/or the patient 224 to upload information onto the remote cloud system 302, download information from the remote cloud system 302 onto one or more of the local information systems 312, 314 and/or perform other actions. The example models 322 include underlying data structures that include and/or organize information used by the views 318 to populate the user interfaces. The example controllers 320 request data from the service tier 306, update the models 322 and/or information employed by the models 322 and instruct the views 318 to adjust or change a presentation (e.g., change a screen, scroll, and/or any other adjustment or change to a presentation) provided via the user interfaces.

The example service tier 306 includes notification services 324, event based services 326, 328 employing a publishing-subscribing messaging model, application or web services 330, data services 332, identity management services 334 and/or other services. The example storage tier 308 includes a plurality of storage devices 336, 338, 340 (e.g., databases, blobs, image management and storage devices, and/or any other storage devices). The example notification services 324 generate and communicate (e.g., via email, text message and/or any other way) notifications to users of the example cloud-based clinical information system 100. For example, if the clinician 234 is referred a case via the cloud-based clinical information system 100, the notification services 324 may generate and communicate a text message to a phone associated with the clinician 234 that indicates that information related to the case is accessible via the cloud-based clinical information system 100. The example application services 330 and the identity management services 334 cooperate to provide and/or verify user credentials and/or manage rights associated with healthcare entities, register healthcare entities with the cloud-based clinical information system, enroll healthcare entities with other healthcare entities and/or manage rules related to the healthcare entities accessing and sharing information via the cloud-based clinical information system 100, and/or perform other actions. In some examples, the application services 330 and/or the identity management services 334 implement a registration manager to assign credentials to a healthcare entity to enable the healthcare entity to employ the cloud-based clinical information system 100. In some examples, the credentials grant the healthcare entity access rights and sharing rights to access and share, respectively, healthcare information associated with the healthcare entity via the cloud-based clinical information system. In some examples, the first access rights and the first sharing rights are based on which type of entity is the healthcare entity. For example, if the healthcare entity is registered as a patient, the application services 330 and/or the identity management services 334 may prevent the user from accessing information related to other patients.

In some examples, the application services 330 and/or the identity management services 334 implement an agreement manager to store a contractual agreement between two or more healthcare entities. In some examples, the application services 330 and/or the identity management services 334 implement an enrollment manager to assign rules to a first healthcare entity defining a least one of access rights or sharing rights to healthcare information associated with a second healthcare entity. In some examples, the access or sharing rights are based on the contractual agreement and one or more selections by a user associated with the second healthcare entity. For example, the user associated with the second healthcare entity may prevent the first healthcare entity from sharing the healthcare information, specify which healthcare entities the first healthcare entity may share the health information with via the cloud-based clinical information system, and/or select other access and/or sharing rights. In some examples, the user interface tier 304 and the service tier 306 interact asynchronously. For example, the controllers 320 may communicate a request for information stored in an image management and storage device (e.g., storage device 340) via the data services 332, and the request may be input into a worklist or queue of the service tier 306. Other architectures are used in other examples.

As described in conjunction with FIG. 1 above, the example cloud-based clinical information system 100 may be used to share information between healthcare entities such as the patient 224 and the site 210. For example, the clinician 234 may prepare a medical report and upload the medical report onto the remote cloud system 302 via a user interface generated by the example user interface tier 304. The example notification services 324 may notify the patient 224 that the report is accessible via the cloud-based clinical information system 100, and the patient may use a web browser to view the report via a zero footprint viewer generated by the views 318. In some examples, the application services 330 implements a case history generator to generate a case history related to a patient. For example, the case history generator may attach healthcare information such as a medical report, a message generated by a clinician, etc. to one or more records and/or other healthcare information related to the patient to generate a case history. In some examples, the case history generator attaches information uploaded from a plurality of healthcare entities to a patient record to generate a case history.

In some examples, the cloud-based clinical information system 100 is a hybrid cloud system including the remote cloud system 302 and a local cloud system 342. For example, the cloud-based clinical information system 100 may enable the site 210 to share information with unaffiliated healthcare entities via the remote cloud system 302 and share information with affiliated healthcare entities via the local cloud system 342 and/or the remote cloud system 302. In some examples, the remote cloud system 302 and the local cloud system 342 are hierarchal. For example, the cloud-based clinical information system 100 may allocate or divide tasks, information, etc. between the remote cloud system 302 and the local cloud system 342 based on resources and/or data availability, confidentiality, expertise, content of information, a type of clinical case associated with the information, a source of the information, a destination of the information, and/or or other factors or characteristics. Some example cloud-based clinical information systems do not employ the local cloud system 342.

The example local cloud system 342 of FIG. 3 is implemented by the example edge device 310. In some examples, the edge device 310 employs a substantially similar architecture to the example architecture 300 of the remote cloud system 302 of FIG. 3 to implement the example local cloud system 342. Thus, the example local cloud system 342 may generate user interfaces, perform notification services, manage and store data, and/or perform other actions and/or services that can be used by healthcare entities affiliated with the site 210. In some examples, the local cloud system 342 functions as a backup to the remote cloud system 302 with respect to information related to the site 210 and/or function as a backup to the local information systems 312, 314. In some examples, the local cloud system 342 employs a different architecture than the architecture 300 of the remote cloud system 302 and/or performs different services than the remote cloud system 302.

In some examples, the edge device uploads information from the local information systems 312, 314 to the local cloud system 342 and/or the remote cloud system 302. In some examples, the edge device 310 analyzes information generated by, stored in and/or used by the local information systems 312, 314 and determines which information is to be uploaded onto the remote cloud system 302 and/or which information is to be uploaded onto the local cloud system 342. In some examples, the edge device 310 determines that information is to be uploaded in only one of the remote cloud system 302 or the local cloud system 342. In some examples, the edge device 310 determines that information is to be uploaded to both the remote cloud system 302 and the local cloud system 342. In some examples, information from the local information systems 312, 314 and/or from the affiliated healthcare entities is routed through the example edge device 310 to enable the edge device to analyze the information to determine if the information is to be uploaded onto the remote cloud system 302 and/or the local cloud system 342.

In some examples, information is uploaded onto the local cloud system 342 based a type of the information and/or content of the information. For example, the edge device 310 may monitor information stored in and/or used by the local information systems 312, 314 and/or communicated between the site 210 and affiliated healthcare entity(ies) to determine types and/or content of information and, based on the types and/or content of information, upload the information onto the remote cloud system 302 and/or local cloud system 342. For example, information related to clinical care of patients may be uploaded and stored in the local cloud system 342. In some examples, the information is stored in the local cloud system 342 temporarily. For example, if a patient is undergoing a surgical procedure at the site 210, information related to the surgical procedure and the patient may be stored in the local cloud system 342 and accessible via the local cloud system 342 throughout the surgical procedure. Following the surgical procedure, the information may be removed from the local cloud system 342 and/or forwarded to the remote cloud system 302. In some examples, information that is to be used only by healthcare personnel at the site 210 is stored in the local cloud system 342. For example, information related to internal policies of the site 210 may be stored in the local cloud system 342. In other examples, information is uploaded onto the local cloud system 342 for other reasons and/or based on other factors and/or determinations.

In some examples, information is uploaded onto the remote cloud system 302 based on a type of information. For example, information to be accumulated for clinical analysis (e.g., as part of a long-term study) may be uploaded onto the remote cloud system 302. In some example, information to be accessible to healthcare entities other than the site 210 is uploaded onto the remote cloud system 302 by the edge device 310. For example, if the clinician 234 refers a patient to another healthcare entity via the cloud-based clinical information system 100, the edge device 310 retrieves information related to the patient from the local information systems 312, 314 and uploads the information to the remote cloud system 302. In other examples, the edge device 310 uploads information to the remote cloud system 302 for other reasons and/or based on other factors and/or determinations.

In some examples, the edge device 310 uploads information onto the remote cloud system 302 and/or the local cloud 310 based a case type associated with the information and/or a business and/or legal relationship between a source of the information (e.g., the site 210) and a destination of the information (e.g., an affiliated healthcare entity or an unaffiliated healthcare entity). Case types include, for example, a trauma case, a specialty case (e.g., an oncology case), a second opinion case, a clearing house case, an image distribution case, a patient referral case, a foreign study management case, a remote interpretation case, a specialty treatment planning case, a review board case, a teaching case, a research exchange case and/or other case types. As described in greater detail below in conjunction with FIG. 7, the edge device 310 may determine if healthcare entities are affiliated or unaffiliated based on business and/or legal agreements uploaded, managed and/or utilized by the example remote cloud system 302 and/or the example local cloud system 342 that are used to establish credentials, access rights and/or sharing rights, and/or the privileges for the healthcare entities via the cloud-based clinical information system 100.

A trauma case arises when the clinician 234 is treating a patient in need of a higher level of trauma treatment that is not available at the site 210. The clinician 234 sends the patient to a healthcare facility with higher trauma treatment capabilities and shares information related to the patient with a clinician at the healthcare facility via the cloud-based clinical information system 100. In some examples, the information related to the trauma case is uploaded onto the local cloud system 342 by the edge device 310 and not uploaded onto the remote cloud system 302 if the healthcare facility is affiliated with the site 210 to conserve time and/or costs associated with bandwidth usage. In some examples, the edge device 210 uploads the information related to the trauma case onto the local cloud system 342 and the remote cloud system 302.

A specialty case arises when the clinician 234 is treating a patient in need of specialty treatment not available at the site 210. The clinician 234 sends the patient to another healthcare facility that provides the specialty treatment and shares information related to the specialty case to a clinician at the other healthcare facility via the hybrid cloud system. In some examples, the information is uploaded onto local cloud system 342 by the edge device 310 if the healthcare facility is affiliated with the site to conserve time and/or costs associated with bandwidth usage. In some examples, the edge device 310 uploads the information related to the specialty case onto the local cloud system 342 and the remote cloud system 302.

A second opinion case arises when the clinician 234 has diagnosed a patient and would like to receive affirmation of the diagnosis from a clinician located at another healthcare facility. The clinician 234 shares information related to the second opinion case to a clinician at the other healthcare facility via the cloud-based clinical information system 100. In some examples, the information is uploaded onto local cloud system 342 by the edge device 310 if the healthcare facility is affiliated with the site 210 to conserve time and/or costs associated with bandwidth usage, but the edge device 310 does not upload the information onto the remote cloud system 302 unless instructed by the clinician 234.

A clearing house case arises when the site 210 sends information related to a plurality of cases to a clearing house healthcare entity to standardize case demographics and/or other clinical characteristic to enable ingestion of the information into the site 210. In some examples, if the clearing house healthcare entity is affiliated with the site 210, the information is shared via the cloud-based clinical information system 100, and the edge device 310 uploads the information onto the local cloud system 342 and not onto the remote cloud system 302. In some examples, the local cloud system 342 performs demographic standardization of the information and enables the clinician 234 and/or other healthcare professionals to view the information via a zero footprint viewer.

An image distribution case arises when the site 210 sends information to a generic healthcare entity that will be accessed by a group of clinicians or users remotely providing case review. If the generic healthcare entity is affiliated with the site 210, the edge device 310 shares the information via the local cloud system 342.

A patient referral case arises when the clinician 234 is a general practitioner and requests a specialist to review a patient case through an affiliated, disconnected network. In some examples, the edge device 310 shares information related to the patient case to the specialist via the local cloud system 342 and not via the remote cloud system 302. In some examples, the edge device 310 shares the information via the local cloud system 342 and uploads the information onto the remote cloud system 302.

A foreign study management case arises when the site 210 receives a large volume of cases involving studies that are to be managed, routed and/or classified to enable the studies to be ingested by one or more of the local information systems 312, 314. In some examples, the information is received via one or more portable storage devices (e.g., compact disks). When the information is ingested from the portable storage device(s), the edge device 310 shares the information via the local cloud system 342 to conserve time and/or reduce costs associated with bandwidth usage. In some examples, the edge device 310 shares the information via the local cloud system 342 and uploads the information onto the remote cloud system 302 based on criteria such as department affiliation, traffic volume, referring source, availability of a patient portal and/or patient request, and/or other criteria.

A remote interpretation case arises when a clinician in a remote or rural geographic location requests an expert at the site 210 to interpret a patient case. If the clinician and the site 210 are unaffiliated, the clinician shares the information via the remote cloud system 302 and not via the local cloud system 342.

A specialty treatment planning case arises when a patient case involves a patient having a chronic disease that warrants planning services and a treatment plan from a specialized facility. The clinician 234 may send the patient to another healthcare facility that provides the planning services and shares information related to the specialty treatment planning case to a clinician at the other healthcare facility via the cloud-based clinical information system 100. In some examples, the information is uploaded onto local cloud system 342 by the edge device 310 if the healthcare facility is affiliated with the site 210 to conserve time and/or costs associated with bandwidth usage. In some examples, the edge device 310 uploads the information related to the specialty case onto the local cloud system 342 and the remote cloud system 302.

A review board case arises when the site 210 sends a patient case to a review board (e.g., a tumor review board) to enable members of the review board to review the patient case. In some examples, the review board employs an edge device to manage information traffic between the members and traffic between the review board and the site 210. In some examples, if the review board and the site are affiliated, the edge device 310 shares information related to the patient case via the local cloud system 342. A teaching case arises when the site 210 shares a patient case suitable for education or instruction to a healthcare entity for repository and/or to be viewed by students or healthcare professionals. In some examples, the edge device 310 anonymizes the patient case and shares the patient case to affiliated healthcare entities via the local cloud system 342 and unaffiliated healthcare entities via the remote cloud system 302. In some examples, the edge device 310 distributes teaching cases between the remote cloud system 302 and the local cloud system 342 based on contributors of the teaching cases, students to be taught based on the teaching case, type of teaching case (e.g., modality, medical phenomena, procedure, etc.).

A research case arises when a researcher at the site 210 shares a case with a colleague prior to submission of a medical paper or article. In some examples, the edge device 310 shares the patient case to affiliated healthcare entities via the local cloud system 342 and unaffiliated healthcare entities via the remote cloud system 302.

Figure 4:
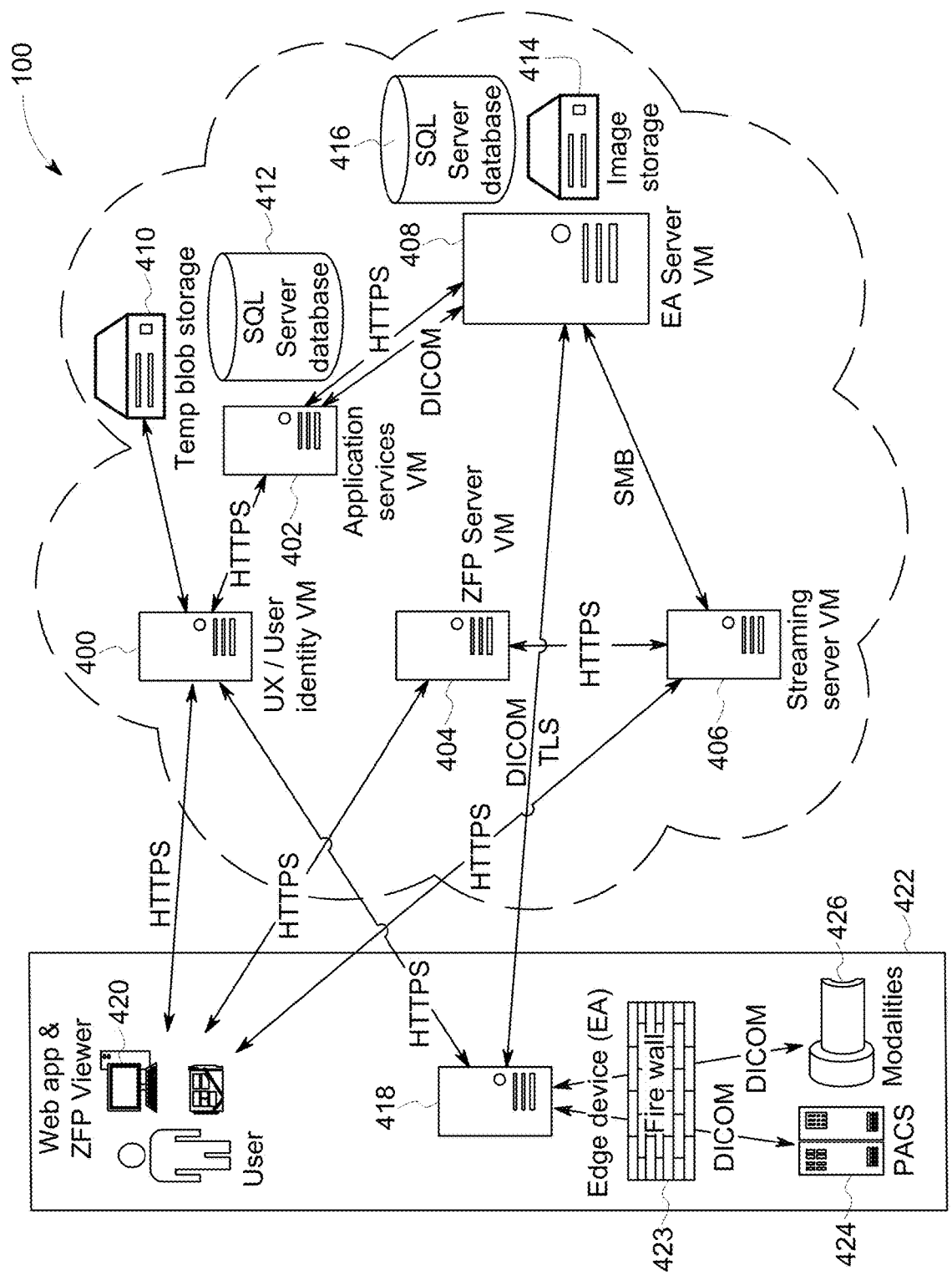
FIG. 4 illustrates an example architecture that may be used to implement the example cloud-based clinical information system of FIG. 1.

FIG. 4 illustrates an example implementation of the example cloud-based clinical information system 100 of FIG. 3. In the illustrated example, the remote cloud system 302 includes a user experience virtual machine 400, an application services virtual machine 402, a zero footprint server virtual machine 404, a streaming server virtual machine 406, an image storage and management virtual machine 408 and a plurality of storage devices 410, 412, 414, 416 in communication with an edge device 418 and a viewer 420 (e.g., a workstation having a web browser) of a site 422 such as a hospital. In the illustrated example, a firewall 423 controls information traffic between the edge device 418 and a PACS 424 of the site 422 and between the edge device 418 and modalities 426 of the site 422.

In the illustrated example, functions of the user interface tier 304, the application services 330 and the identify management services 334 are performed via the user experience virtual machine 400. Functions of the notification services 324, the event based services 326, 328 and the data services 306 are performed via the example application services virtual machine 402. The example zero footprint virtual machine 404 is used to perform functions of the user interface tier 304 such as rendering views or presentations, populating the views, providing user tools within the views, and/or other functions. The example streaming server virtual machine 406 retrieves information from, for example, the storage device 336, 338, 340 to populate views generated by the user interface tier 304. The example image management and storage virtual machine 408 is used to manage information flow between the storage devices 336, 338, 340 and one or more of the edge device 418, the application services virtual machine 402, and the streaming server virtual machine 406.

Figure 5:
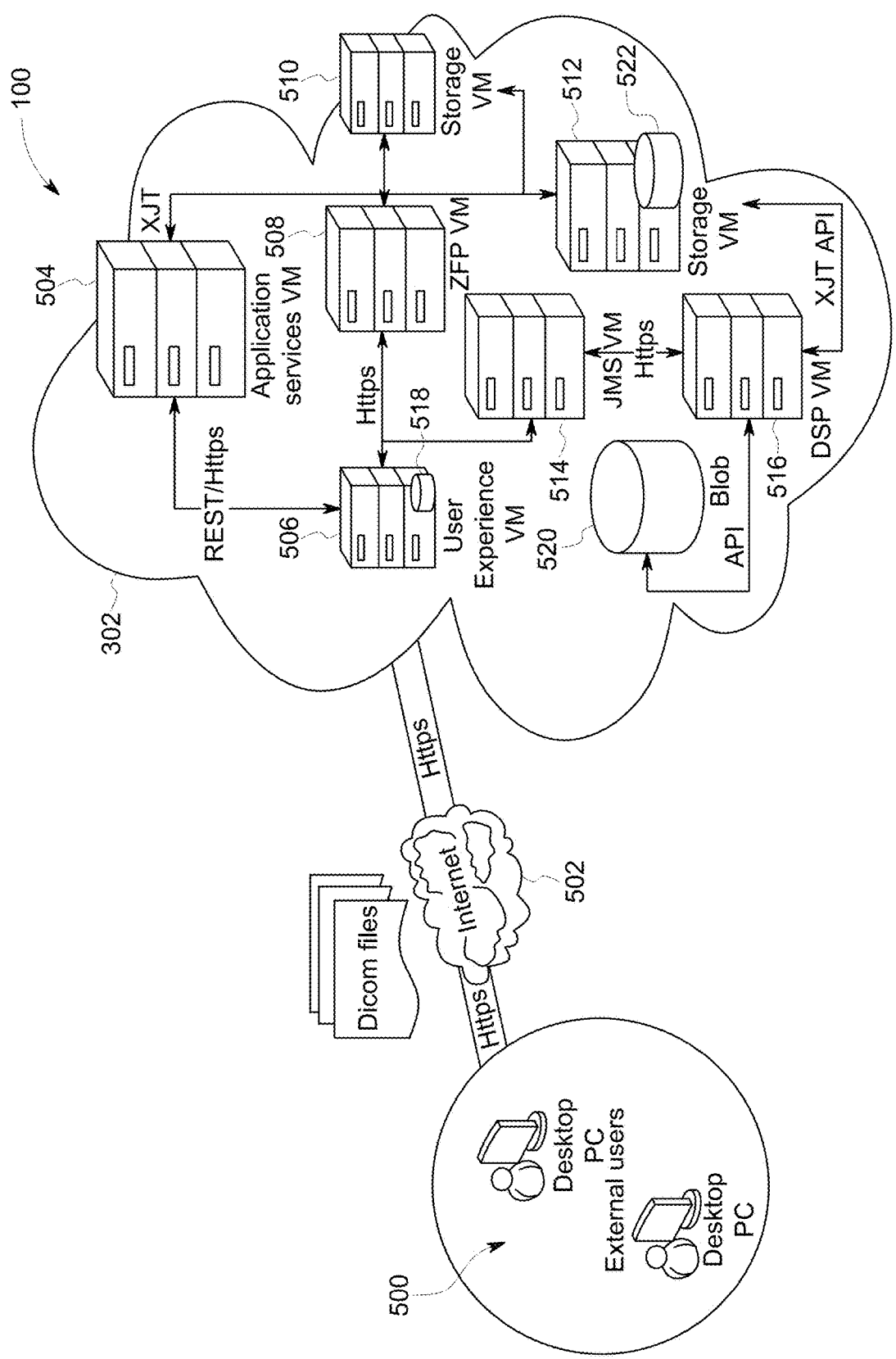
FIG. 5 illustrates an example architecture that may be used to implement the example cloud-based clinical information system of FIG. 1.

FIG. 5 illustrates another example implementation of the example cloud-based clinical information system 100. In the illustrated example, a plurality of healthcare entities 500 are in communication with the cloud 300 via the internet 502. The example cloud 300 includes an application services virtual machine 504, a user experience virtual machine 506, a zero footprint viewer virtual machine 508, information management and storage virtual machines 510, 512, a JMS virtual machine 514, a DSP virtual machine 516 and a plurality of storage devices 518, 520, 522. In some examples, functions of the example application services 330 and/or the identity management services 334 such as verifying user credentials and/or managing rules related to receiving and sharing information via the credentials are performed via the application services virtual machine 504. In some examples, functions of the user interface tier 304, the application services 330 and the identify management services 334 are performed via the user experience virtual machine 506. The example zero footprint virtual machine 508 is used to perform functions of the user interface tier 304 such as rendering views or presentations, populating the views, providing user tools within the views, and/or other functions. In some examples, functions of the notification services 324, the event based services 326, 328 and the data services 306 are performed via the example JMS virtual machine 514 and/or the DSP virtual machine 516. The example information management and storage virtual machines 510, 512 are used to manage information flow within the example remote cloud system 302 of FIG. 5.

Flow diagrams representative of example machine readable instructions for implementing the example cloud-based clinical system 100 are shown in FIGS. 6-8 and 15-22. In these examples, the machine readable instructions comprise a program for execution by a processor such as the processor 2312 shown in the example processor platform 2300 discussed below in connection with FIG. 23. The program may be embodied in software stored on a tangible computer readable storage medium such as a CD-ROM, a floppy disk, a hard drive, a digital versatile disk (DVD), a Blu-ray disk, or a memory associated with the processor 2312, but the entire program and/or parts thereof could alternatively be executed by a device other than the processor 2312 and/or embodied in firmware or dedicated hardware. Further, although the example programs are described with reference to the flowcharts illustrated in FIGS. 6-8 and 15-22, many other methods of implementing the example cloud-based clinical information system 100 may alternatively be used. For example, the order of execution of the blocks may be changed, and/or some of the blocks described may be changed, eliminated, or combined.

As mentioned above, the example processes of FIGS. 6-8 and 15-22 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of FIGS. 6-8 and 15-22 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

Figure 6:
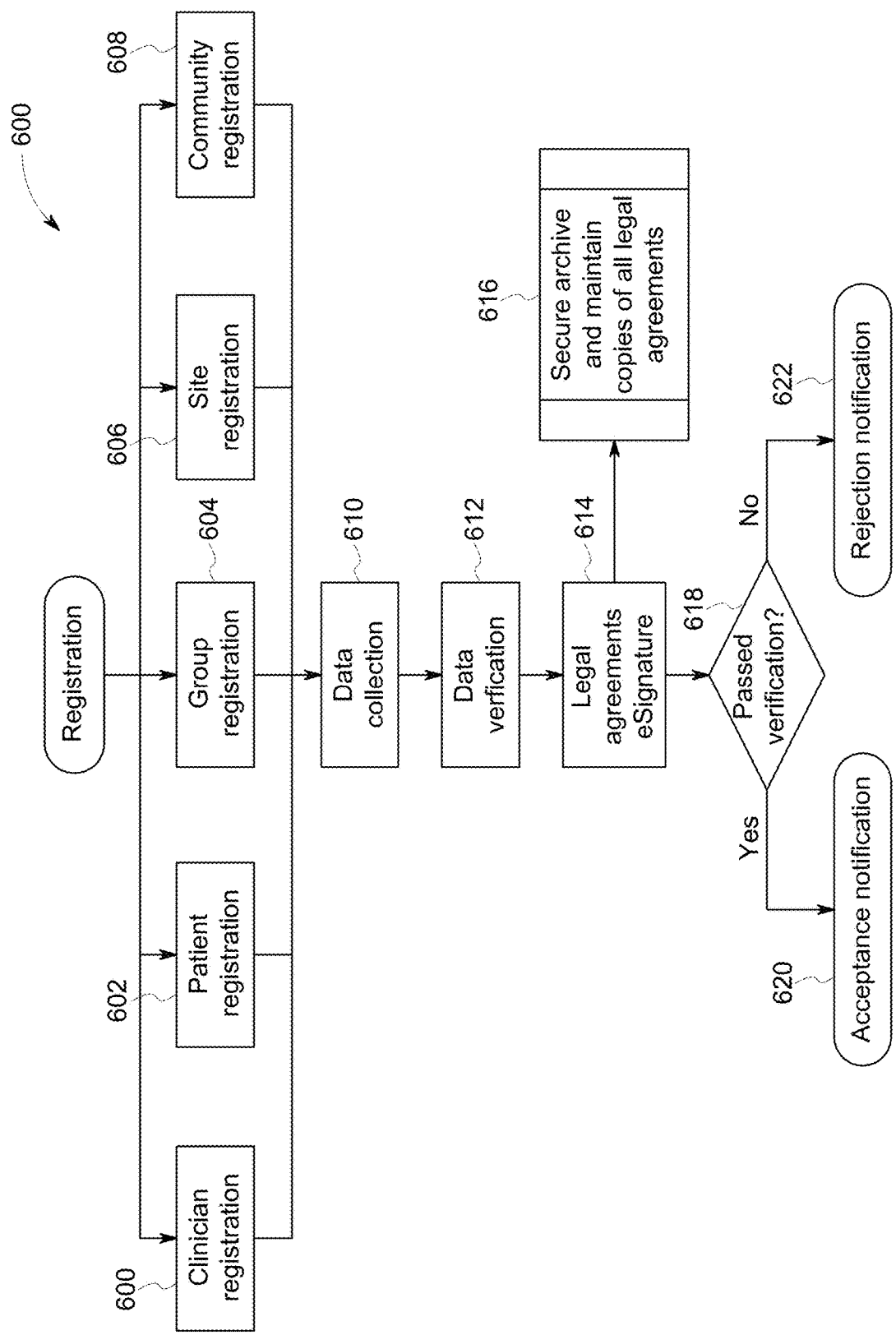
FIG. 6 is a flow diagram illustrating an example workflow to register a healthcare entity with the example cloud-based clinical information system.

FIG. 6 illustrates a flow diagram of workflow 600 for an healthcare entity to register with the example cloud-based clinical information system 100. In some examples, the healthcare entity registers with the example cloud-based clinical information system 100 to create a profile or persona for use with the cloud-based information system 100 and/or acquire credentials associated with one or more of the entity types. In the illustrated example, the healthcare entity selects one of a plurality of registration paths 600, 602, 604, 606, 608 corresponding to a respective one of a plurality of entity types. The example workflow 600 of FIG. 6 includes clinical registration 600, patient registration 602, group registration 604, site registration 606 and community registration 608.

At block 610, data is collected based on the one of the registration paths 600, 602, 604, 606, 608 selected by the healthcare entity. For example, a clinician registering with the example cloud-based clinical information system 100 may input information such as, name, address, title, phone number, pager number, license number, email address, preferred notification method, group affiliation, site affiliation, clinician identification (e.g., user name) and password and/or other information. In some examples, the clinician consents to terms of use of the example cloud-based clinical information system 100, electronically executes business associate agreements, protected health information agreements and/or other agreements and/or contracts.

A group registering with the example cloud-based clinical information system 100 may input information such as group name, group address, group administrator information (e.g., name, address, title, phone number, email address, username and password, and/or other information) and/or other information. In some examples, the group consents to terms of use of the example cloud-based clinical information system 100, electronically executes business associate agreements, protected health information agreements and/or other agreements and/or contracts. In some examples, the group inputs information related to affiliations with sites and/or other healthcare entities.

A site registering with the example cloud-based clinical information system 100 may input information such as site name, site address, account and/or billing information, site administrator information, and/or other information. In some examples, the site consents to terms of use of the example cloud-based clinical information system 100, electronically executes business associate agreements, protected health information agreements and/or other agreements and/or contracts. In some examples, the site inputs information related to affiliations with other healthcare entities. In some examples, the site also inputs information related to local information systems employed by the site. For example, the site may input information related to PACS that are in communication with an edge device (e.g., the edge device 310).

In some examples, a community is registered via an administrator of the example cloud-based clinical information system 100. For example, the administrator of the cloud-based clinical information system 100 may register a community based on a request from business and/or commercial leaders in a geographic region and/or a subject matter area. In some examples, the administrator inputs information related to the community to register the community such as a name and/or contact information of the administrator, business and/or commercial leader contact information and/or other information.

A patient registering with the example cloud-based clinical information system 100 inputs information related to the patient such as name, address, contact information, username, password and/or other information. In some examples, the patient consents to terms of use of the example cloud-based clinical information system 100 and/or other agreements and/or contracts.

At block 612, the cloud-based clinical information system 100 facilitates verification of the data input by the healthcare entities registering with the example cloud-based clinical information system 100. For example, the cloud-based clinical information system 100 may verify information input by a clinician by comparing the information input by the clinician to information stored in a database employed by the example cloud-based clinical information system 100. In some examples, information input by a group is verified by an administrator of a site employing the example cloud-based clinical information system 100. In some examples, an administrator verifies information input by a community. In other examples, information is verified in other ways.

At block 614, agreements electronically executed by the healthcare entities registering with the example cloud-based clinical information system are stored in a secure archive 616. If the information input by one of the healthcare entities is verified at block 618, an acceptance notification is communicated (e.g., via email) to the healthcare entity at block 620, and the healthcare entity is registered with the example cloud-based clinical information system 100. Thus, the healthcare entity may access and use the example cloud-based clinical information system 100. If the information is not verified, a rejection notification is communicated to the healthcare entity at block 622, and the healthcare entity is not registered. In some examples, the rejection notification includes an explanation indicating why the information was not verified.

Figure 7:
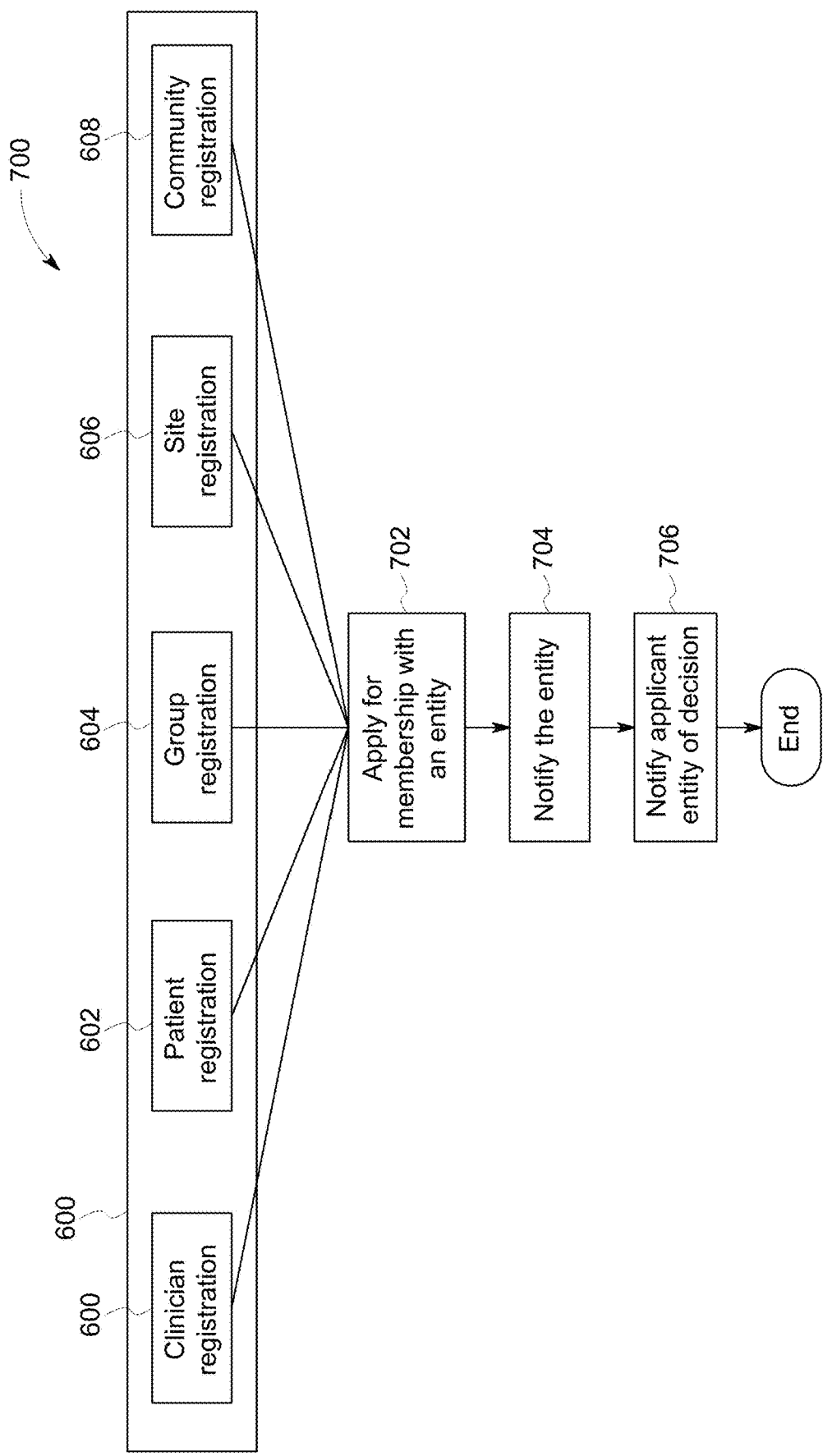
FIG. 7 is a flow diagram illustrating an example workflow to enroll a first healthcare entity with a second healthcare entity to enable the first healthcare entity and the second healthcare entity to share information via the example cloud-based clinical information system of FIG. 1.

FIG. 7 illustrates a flow diagram of an example workflow 700 to enroll a first healthcare entity with a second healthcare entity. Once the first healthcare entity is registered with the example cloud-based clinical information system 100 (e.g., using the example workflow 600 of FIG. 6), the first healthcare entity may access and use the cloud-based clinical information system 100. However, to access information from the second healthcare entity, the first healthcare entity enrolls with the second healthcare entity. In the illustrated example, enrollment involves requesting membership with the second healthcare entity and receiving approval from the second healthcare entity.

At block 702, the first healthcare entity applies for membership with the second healthcare entity. In some examples, the first healthcare entity applies via a user interface generated by the example cloud-based clinical information system 100. In some examples, the user interface enables the first healthcare entity to search for the second healthcare entity via a directory. The first healthcare entity may then select the second healthcare entity to apply for membership with the second healthcare entity. In some examples, the first healthcare entity may request privileges to one or more local information systems of the second healthcare entity. For example, if the first healthcare entity is a clinician, the first healthcare entity may request Promote-To-PACS privileges of a PACS of the second healthcare entity.

In some examples, when the first healthcare entity applies for membership with the second healthcare entity, the cloud-based clinical information system 100 determines if a business and/or legal agreement exists between the first healthcare entity and the second healthcare entity. For example, the cloud-based clinical information system 100 determines if the first healthcare entity and the second healthcare entity are affiliated by determining if an agreement is stored in a database employed by the example cloud-based clinical information system 100. If the first healthcare entity and the second healthcare entity are not affiliated, the first healthcare entity is provided with an agreement and/or terms of use of the second healthcare entity via the cloud-based clinical information system 100. The agreement may be generated by the example cloud-based clinical information system 100 and/or the second healthcare entity. In some examples, the agreement and/or terms of use governs and/or determines rules for the first healthcare entity to access and/or share information accessible from the second healthcare entity via the cloud-based clinical information system 100. For example, the agreement and/or terms of use may specify that the first healthcare entity may only use information from the second healthcare entity in predetermined ways and/or for predetermined purposes. In some examples, the agreement and/or terms of use governs which healthcare entities the first healthcare entity may share information with via the cloud-based clinical information system 100. For example, the agreement and/or terms of use may enable the first healthcare entity to refer patients under the care of the second healthcare entity to predetermined healthcare entities via the cloud-based clinical information system 100 while preventing the first healthcare entity from referring patients to healthcare entities unaffiliated with the second healthcare entity via the cloud-based clinical information system 100. In some examples, the example cloud-based clinical information system 100 stores the terms of use and/or the agreements and sets or writes rules for the first healthcare entity to access and share information via the cloud-based information system 100 based on the agreements and/or terms of use.

In some examples, the cloud-based clinical information system 100 enables the first to enroll with only predetermined healthcare entity types based on the example hierarchal organization scheme 200 of FIG. 2. For example, if the first healthcare entity is registered as a clinician, the first healthcare entity may enroll with groups, sites, IDNs and communities. However, the first healthcare entity may not enroll with patients. In another example, if the first healthcare entity is registered as a site, the first healthcare entity may enroll with IDNs and communities but not with clinicians.

Once the first healthcare entity applies for membership with the second healthcare entity at block 702, the cloud-based clinical information system 100 notifies the second healthcare entity. In some examples, the cloud-based clinical information system 100 queues an application of the first healthcare entity for membership in a worklist of the second healthcare entity and sends an email to an administrator of the second healthcare entity to notify the administrator of the application. The second healthcare entity may then review the application and approve and/or reject the application. At block 706, the first healthcare entity is notified of the decision of the second healthcare entity. If the second healthcare entity approved the application, the first healthcare entity may access information from the second healthcare entity via the cloud-based clinical information system 100.

Figure 8:
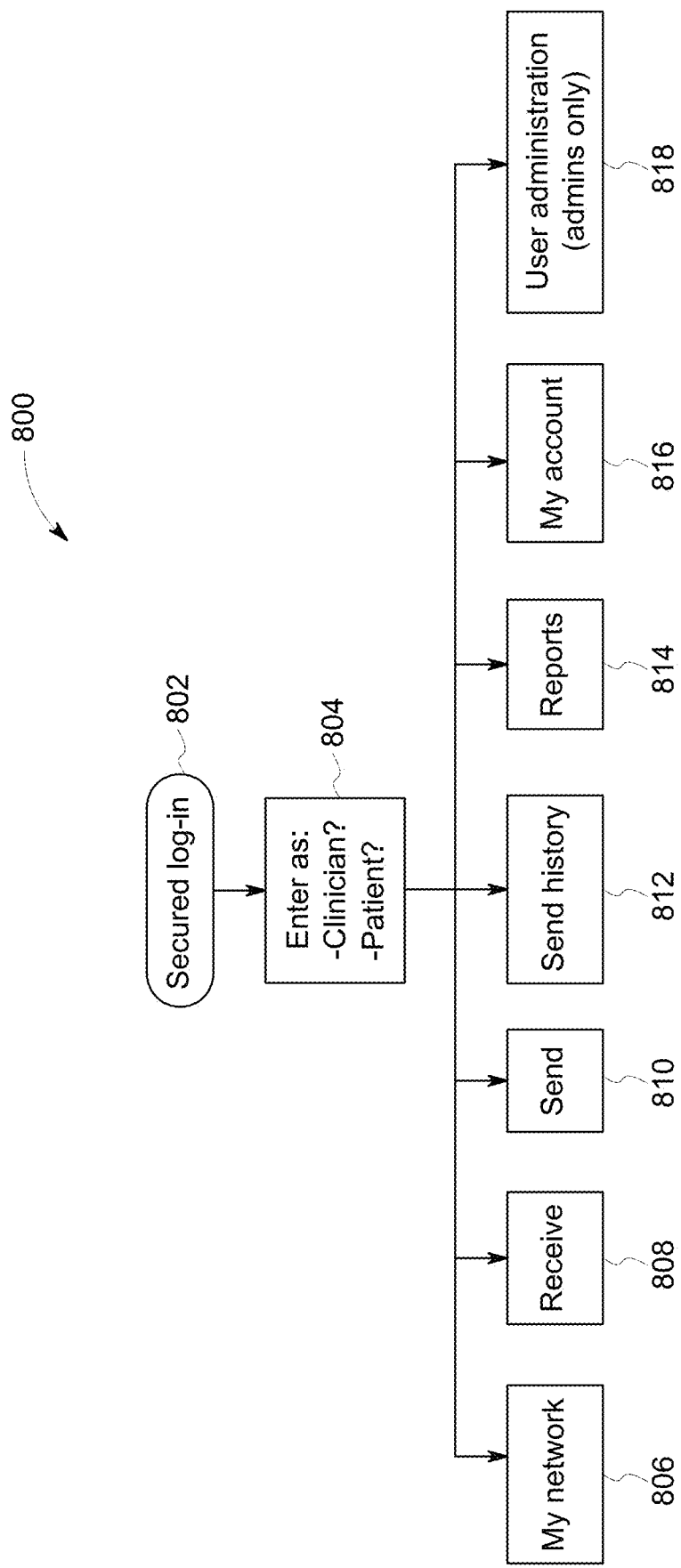
FIG. 8 is a flow diagram illustrating an example workflow of an example user interface which may be used to implement the example cloud-based clinical information system of FIG. 1.

FIG. 8 illustrates a flow diagram of an example user interface workflow 800 disclosed herein. In the illustrated example, at block 802, a user may access a user interface generated via the example cloud-based clinical information system 100 via a web browser and securely log-in to the cloud-based clinical information system 100 using a username and password input during registration (FIG. 6) of a healthcare entity associated with the user. In some examples, if the user is associated with two entity types (e.g., the user may be a clinician plus a patient), the user selects one of the two entity types at block 804. Once the user logs in and has access to the user interface, the user may use the user interface to perform a plurality of actions via the cloud-based clinical information system 100. In the illustrated example, the user may view a network at block 806, receive information from a healthcare entity at block 808, send information to a healthcare entity at block 810, send history (e.g., patient information history, transaction history, and/or other histories) to a healthcare entity at block 812, view reports at block 814, manage an account of the user with the cloud-based clinical information system 100 at block 816, perform administration tasks if the user is a healthcare entity administrator at block 818 and/or perform other actions.

For example, once a first healthcare entity is registered with the example cloud-based clinical information system 100 and enrolled with a second healthcare entity, the first healthcare entity may employ the example cloud-based clinical information system to send information to the second healthcare entity via the cloud-based clinical information system 100 and receive information from the second healthcare entity via the cloud-based clinical information system. For example, the first healthcare entity may upload messages, documents, images (e.g., x-rays, etc.) and/or other information onto the remote cloud system 302 to be viewed and/or downloaded by the second healthcare entity. In some examples, the first healthcare entity may share information from a local information system such as a DICOM system or a PACS via the cloud-based clinical information system 100. In some examples, the healthcare entity may share information from a CD or file stored on a local workstation. In some examples, the healthcare entity may employ a one-time share option to share information via the cloud-based clinical information system 100 with an healthcare entity that is not registered with the cloud-based clinical information system 100. In some examples a history may be shared via the example cloud-based clinical information system 100. In some examples, the history includes information of patients previously treated by the healthcare entity, accessed by the healthcare entity, shared by the healthcare entity and/or any other information.

As described above, information may also be received via the example cloud-based clinical information system 100. In the illustrated example, information stored in the remote cloud system 302 may be accessed via email and/or via a portal. For example, a user may receive an email including a URL link to information accessible via the remote cloud system 302 (e.g., sent by a healthcare entity), and the user may employ a web browser to open and display the information. In some examples, the user may log into the cloud-based clinical information system 100 and view the information via a user interface (FIGS. 9-11) such as a zero footprint viewer. In some examples, the information may be downloaded onto a local computer. In some examples, the cloud-based clinical information system 100 ingests data from a portable storage device (e.g., a CD, a thumbdrive, and/or any other portable storage device), a local computer, an information system and/or any storage device.

Figure 9:
FIG. 9 illustrates an example user interface disclosed herein.
Figure 10:
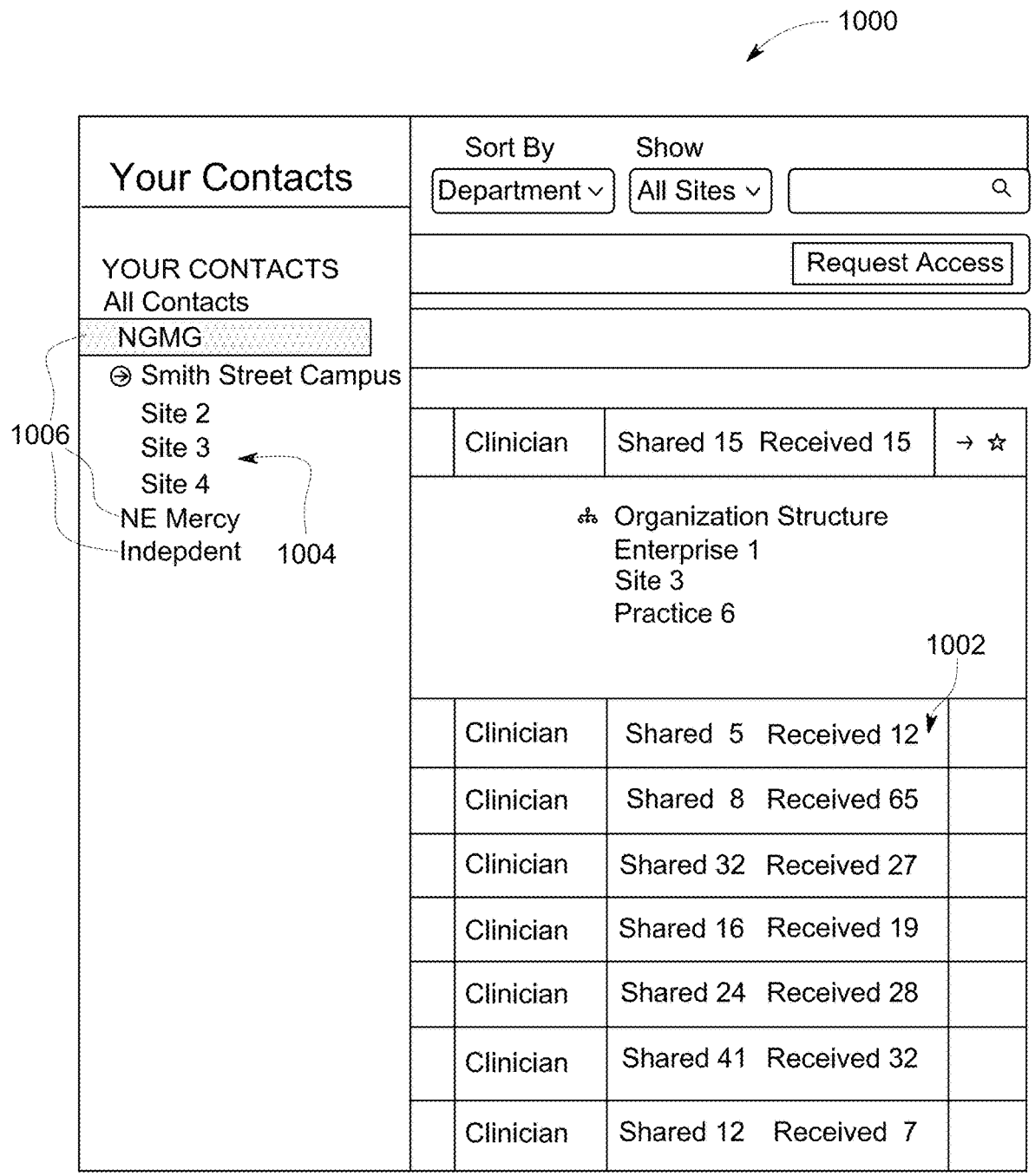
FIG. 10 illustrates an example user interface disclosed herein.

Example user interfaces that may be used to implement the example cloud-based clinical information system 100 and the example workflows 700 and 800 of FIGS. 7-8 are illustrated in FIGS. 9-10. FIG. 9 illustrates an example user interface 900 that may be generated via a web browser and accessed via a secure login by a user (e.g., an administrator of a healthcare entity). In the illustrated example, the user interface 900 lists healthcare entities 902 (e.g., clinicians, groups, sites, communities and/or other healthcare entities) that the user may send information to and/or receive information from via the example cloud-based clinical information system 100 (e.g., the user is enrolled with the healthcare entities 902 and/or the healthcare entities 902 are enrolled with the user). The example user interface 900 also enables the user to send messages to the healthcare entities 902, which may include information retrieved from a local information system (e.g., PACS). In some examples, the user interface 900 enables the user to sort the healthcare entities 902 based on entity type and/or other in other ways (e.g., alphabetically, via tags, by geographic location, by industry, by department, by practice type and/or other ways). In some examples, the user may select a healthcare entity listed on the user interface 900 to view communication between the user and the healthcare entity, view information shared between the user and the healthcare entity, enable the user to share information with the healthcare entity via the cloud-based clinical information system 100, and/or perform other actions. For example, the user may select one of the healthcare entities 900 and view a medical image sent to the user by the one of the healthcare entities 900 using a zero footprint viewer.

In the illustrated example, the user interface 900 enables the user to request enrollment and/or enroll with other healthcare entities. For example, the user may view a directory of healthcare entities and select one or more of the healthcare entities to request enrollment with the healthcare entity(ies). The user interface 900 may automatically populate portions of an application to be submitted by the user to enroll with the healthcare entity with information such as, name, type of entity, geographic information, and/or other information related to the user requesting enrollment. In some examples, the user may search for one or more healthcare entities via the directory based on practice type or specialty (e.g., radiology, pediatrics, etc.), geographic location, name, and/or other characteristic(s) and/or in other ways. In some examples, the directory includes healthcare entities that are registered with the example cloud-based clinical information system but are not affiliated with the user. Thus, the user interface 900 enables the user to expand a network of healthcare professions for referrals, medical expertise, treatment options, etc.

FIG. 10 illustrates another example user interface 1000 disclosed herein that may be used to implement the example cloud-based clinical information system 100. The example user interface of FIG. 10 may be generated via a web browser and accessed via a secure login by a user (e.g., an administrator of a healthcare entity). In the illustrated example, the user interface 1000 lists of healthcare entities including clinicians 1002 that are members of sites 1004 that are members of integrated delivery networks (IDNs) 1006. In some examples, the user may be enrolled with the clinicians 1002 but not the sites 1004 or the IDNs 1006. In some examples, the user interface 1000 enables the user to request enrollment with the sites 1004, the IDNs 1006 and/or members of the sites 1004 (e.g., clinicians) and/or the IDNs (e.g., other sites).

FIG. 11 illustrates an example user interface 1100 that may be used to implement the example cloud-based clinical information system 1100. In the illustrated example, the user interface 1100 enables the user to view an inbox 1101 listing one or more transactions 1102 (e.g., information sent, information received, messages communicated, and/or any other transactions). In some examples, the transactions are organized based on cases. For example, if the user is a clinician, a case may be transactions related to a patient under the care of the user. The user may use the example user interface 1100 to view all cases, view cases created by the user, view cases received by the user, view cases shared by the user, view cases of a selected type, view related cases, view draft cases, preview a case or information (e.g., by placing a cursor over an icon representative of the case or the information) and/or view other types or categories of information. In some examples, the user interface 1100 enables the user to create a new case, share the new case with a healthcare entity via the cloud-based clinical information system 100, adjust account settings, perform a context-sensitive search (e.g., for cases, words in messages, names, etc.), run a report (e.g., analytics, benchmarking, and/or any type of report), perform administrative actions (e.g., change billing information of a site, etc.) and/or perform other actions and/or view other information.

If the user selects one of the cases, the user interface 1100 may display a history of the case. The history may include senders and recipients of the case, rational(s) for sharing the case, forwarding and replying logs, comments related to the case, studies and/or files associated with the cases and/or other information (e.g., dates, times, and/or any other information). In some examples, the interface 1100 enables the user to add information to the case (e.g., comments, reports, analysis, and/or other information), forward the case to one or more healthcare entities (e.g., one of the healthcare entities 902, 1002, 1006, 1008 listed in the user interfaces of FIGS. 9-10), view case information (e.g., medical images, reports, patient information, and/or other information), request information related to the case from other healthcare entities, decline a referral, accept a referral and/or perform other actions.

In some examples, the user interface 1100 enables users to collaborate regarding a case. For example, a first clinician treating a patient may send a case to a second clinician. The second clinician may view patient information such as medical images, reports, case history, comments provided by the first clinician and/or other information via the user interface 1100. The second clinician may analyze the patient information and generate a report including, for example, a clinical analysis, which the second clinician sends to the first clinician via the remote cloud system 302. The cloud-based clinical information system 100 attaches the report to the case, and the first clinician may view the case including the report from the second clinician via the user interface 1100. The first clinician may then use the report to treat the patient.

In some examples, information is accessible via the user interface 1100 for a predetermined amount of time. For example, if the user of the interface 1100 receives a medical image to analyze from a healthcare entity via the cloud-based clinical information system 100, the medical image may be accessed and viewed via the interface 1100 for thirty days from a day of receipt and/or a day on which the medical image was first viewed. After thirty days, the user may no longer be able to view the medical image unless the healthcare entity re-sends the medical image. In some examples, the user interface 1100 provides a zero footprint viewer and automatically populates the viewer with information. For example, if the healthcare entity sends the user the medical image related to a patient, the user interface 1100 may present the image and information related to the patient (e.g., name, date the medical image was captured, etc.) via the zero footprint viewer.

Figure 12:
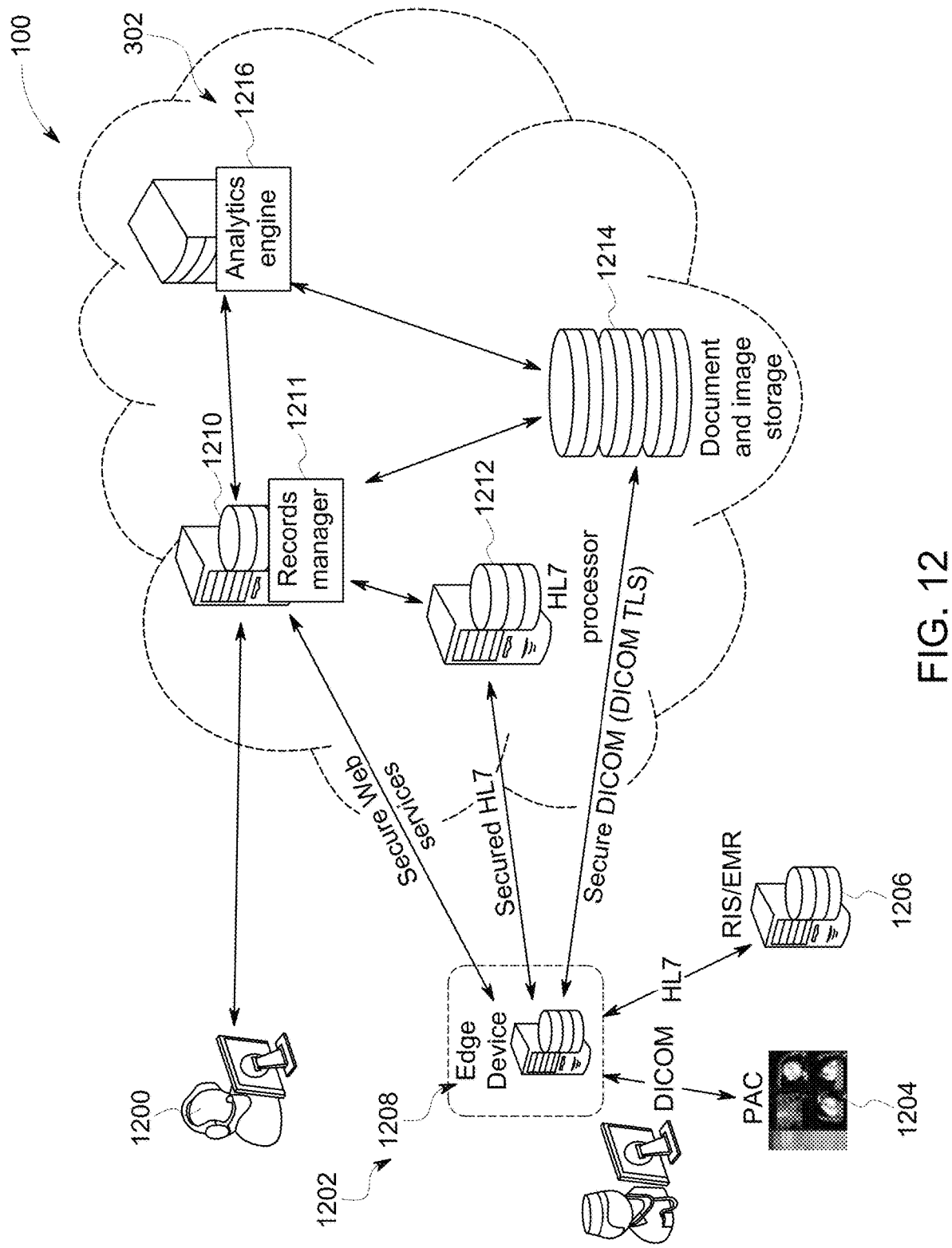
FIG. 12 illustrates the example cloud-based clinical information system employed to integrate a first local information system and a second local information system of a healthcare entity with the cloud-based clinical information system.

FIG. 12 illustrates the example cloud-based clinical information system 100 in communication with a first healthcare entity 1200 and a second healthcare entity 1202. In the illustrated example, the cloud-based clinical information system 100 is integrated with a first local information system 1204 and a second local information system 1206 of a second healthcare entity 1202. In the illustrated example, the second healthcare entity 1202 is a site such as a care center. In the illustrated example, a first healthcare entity 1200 such as a clinic may refer a patient to the second healthcare entity 1202 via the cloud-based clinical information system 100. For example, the first healthcare entity 1200 may use the example user interfaces 900, 1000, 1100 of FIGS. 9-11 to upload information related to the patient (e.g., demographic information such as name, age, etc., medical information such as reports, images such as x-rays and/or other information) onto the cloud-based clinical information system.

In the illustrated example, an edge device 1208 is employed by the example second healthcare entity 1202 to facilitate communication between the first local information system 1204 (e.g., PACS) and the remote cloud system 302 and between the second clinical information system 1202 (e.g., a RIS/EMR system) and the cloud. In other examples, more than one edge device may be employed. The example remote cloud system 302 of FIG. 12 includes a cloud application 1210, records manager 1211, an HL7 processor 1212, document and image storage devices 1214, and an healthcare information analytics engine 1216. As described in greater detail below in conjunction with FIGS. 13-14, the example edge device 1208 and the remote cloud system 302 cooperate to automatically generate patient and/or exam records in the first local information system 1204 and/or the second local information system 1206 when the first healthcare entity 1200 refers the patient to the second healthcare entity 1202.

Figure 13:
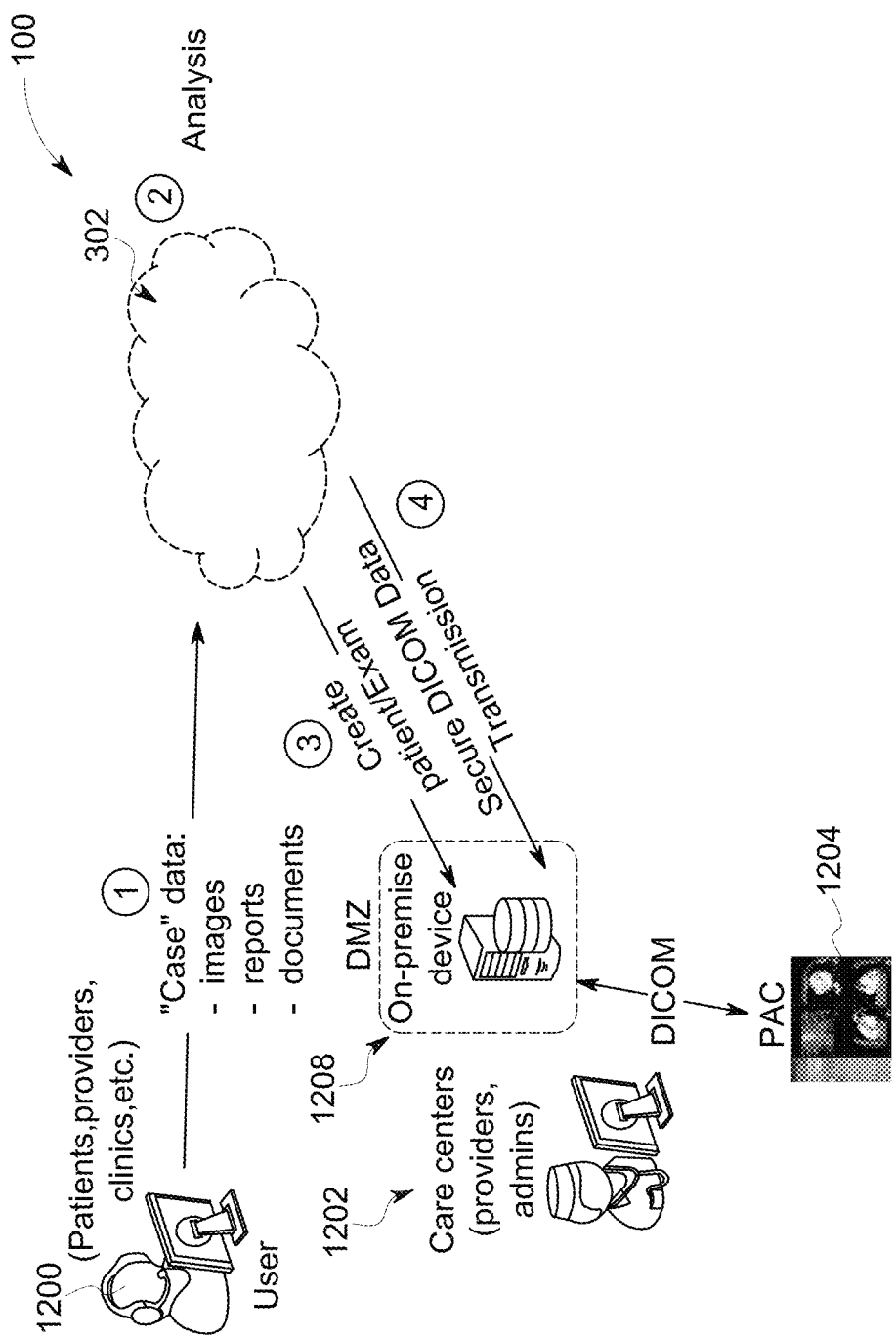
FIG. 13 illustrates an example workflow to automatically generate patient and/or exam records in the first local information system of FIG. 12.

FIG. 13 illustrates an example workflow illustrating the example cloud-based clinical information system 100 integrated with the first local information system 1204 of the first healthcare entity of FIG. 12 to automatically generate a patient record in the first local information system 1204. In the illustrated example, the first local information system 1204 is a PACS employing DICOM protocol. Other examples may use other types of local information systems and/or protocols.

In the illustrated example, the first healthcare entity 1200 refers a patient to the second healthcare entity 1202 by uploading a patient referral order including healthcare information such as images, reports, documents, and/or other information into the document and image storage devices 1214 of the remote cloud system 302 via the cloud application 1210. In some examples, the cloud-based clinical information system 100 notifies the second healthcare entity 1202 (e.g., via an email) of the referral and enables the second healthcare entity 1202 to accept or decline the referral (e.g., via the user interfaces 900, 1000, 1100 of FIGS. 9-11).

The healthcare information analytics engine 1216 of the example cloud-based clinical information system 100 analyzes the case data to determine, for example, that the second healthcare entity 1202 is to receive the case data by, for example, digesting predetermined parameters and/or data. The example cloud-based clinical information system 100 instructs the edge device 1208 to communicate with the first local information system 1204 and automatically generate a patient record (e.g., an exam record) and/or attach the healthcare information to an existing patient record (e.g., a record previously generated in the first local information system 1204, for example, if the patient has been previously treated via the second healthcare entity 1202). The example cloud-based clinical information system 100 then sends the healthcare information via, for example, a Secure DICOM data transmission to the edge device 1208, and the edge device 1208 forwards the healthcare information to the first local information system 1204.

In some examples, the healthcare information analytics engine 1216 determines which portions of the healthcare information such as a medical image is to be stored in the first local information system 1204, and the records manager 1211 separates, tags and/or communicates the portion of the healthcare information to the edge device 1208 via the document and storage devices 1214. The example local information system 1200 then automatically attaches the portion of the healthcare information to the patient record. Thus, before and/or when the example patient is transported and/or arrives at the second healthcare entity 1202 for treatment, the patient record is available to health professionals of the second healthcare entity 1202.

Figure 14:
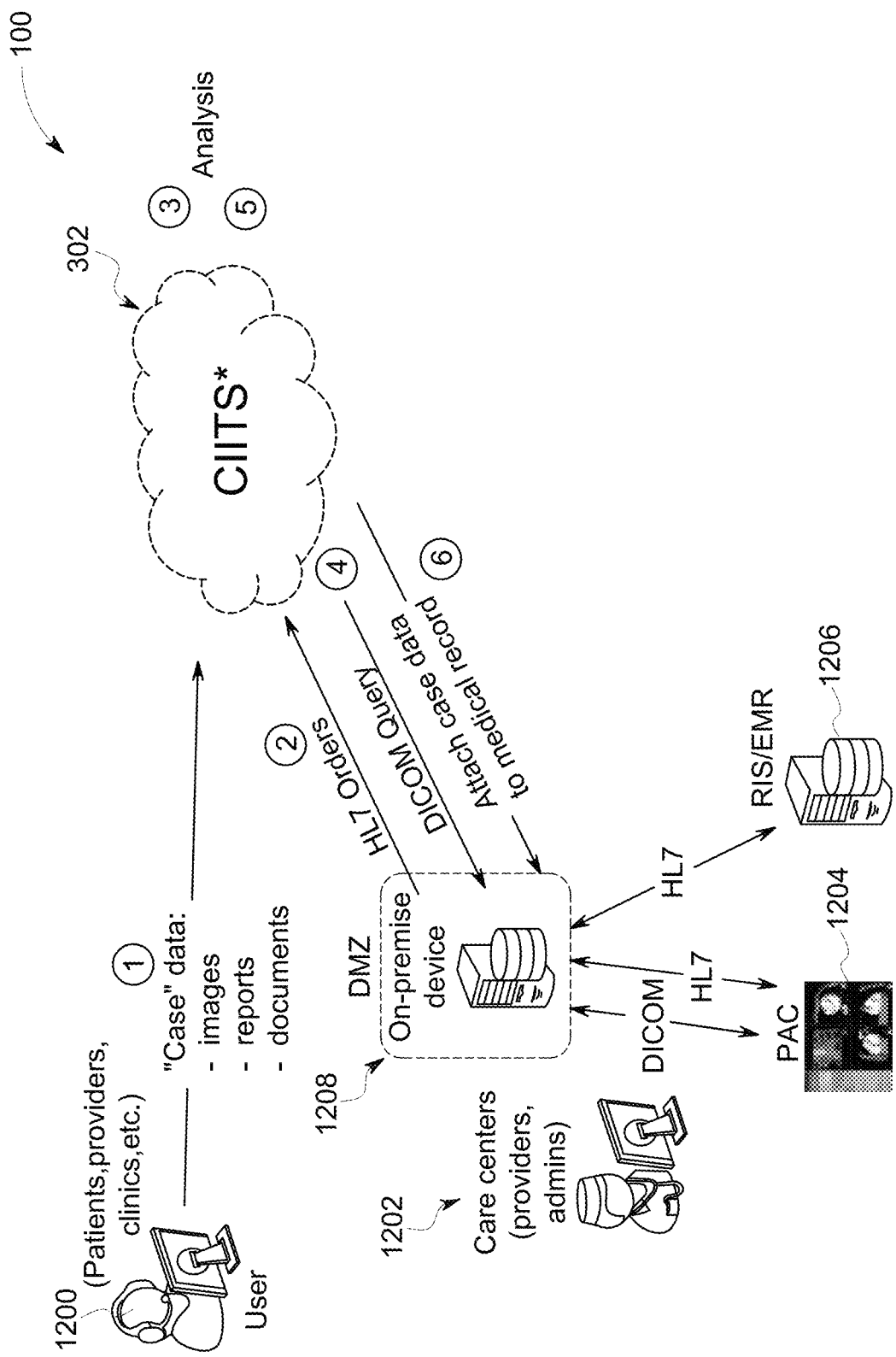
FIG. 14 illustrates an example workflow to automatically generate patient and/or exam records in the first local information system and the second local information system of FIG. 12.

FIG. 14 illustrates an example workflow illustrating the example cloud-based clinical information system 100 integrated with the first local information system 1204 and the second local information system 1206 of the first healthcare entity of FIG. 14 to automatically generate patient records in the first local information system 1204 and/or the second local information system 1204. In the illustrated example, the first local information 1204 is the PACS employing the DICOM protocol and the second local information system 1206 is a radiology information system (RIS) and/or electronic medical records (EMR) system employing HL7 protocol. Other examples employ other types of local information systems and/or protocols.

In some examples, the first healthcare entity 1200 refers a patient to the second healthcare entity 1202 by uploading a patient referral order including, for example, healthcare information such as images, reports, documents, and/or other information into the document and storage devices 1214 of the remote cloud system 302 via the cloud application 1210. In the illustrated example, the cloud-based clinical information system 100 automatically retrieves healthcare information related to the patient uploaded onto the remote cloud system 302 from other healthcare entities employing the cloud-based clinical information system 100 to enable the second healthcare entity 1202 to view and/or store a comprehensive and/or cohesive collection of information related to the patient. For example, the records manager 1211 may search or query the document and image storage device 1214 for healthcare information related to the patient. In some examples, the edge device 1208 requests HL7 order transactions and/or PACS data related to the patient, and the records manager 1211 collects HL7 order transactions related to the patient from other healthcare entities employing the example cloud-based clinical information system 100. In some examples, the cloud-based clinical information system 100 uploads the HL7 order transactions into the remote cloud system 302. Healthcare information from the HL7 order transactions is matched via fuzzy logic via the healthcare information analytics engine 1216. In some examples, the remote cloud system 302 conducts one or more DICOM queries to the first local information system 1204 via the edge device 1208. The example healthcare information analytics engine 1216 of the cloud-based clinical information system 100 analyzes the healthcare information included in the patient referral order, the HL7 order transactions and/or PACS data to determine, for example, which one(s) of the first local information system 1204 and/or the second local information system 1206 is to generate patient records to be populated by one or more portions of the healthcare information.

The example cloud-based clinical information system 100 instructs the edge device 1208 to communicate with the first local information system 1204 and/or the second local information system 1206 to automatically generate patient records and/or attach the healthcare information to existing patient and/or exam records. The example cloud-based clinical information system 100 then sends the healthcare information to the edge device 1208, and the edge device 1208 forwards the healthcare information to the first local information system 1204 and/or the second local information system 1206. The example local information system 1200 and/or the example second local information system 1206 automatically attaches the healthcare information to the patient records. Thus, before and/or when the example patient is transported and/or arrives at the second healthcare entity 1202 for treatment, the patient records are available to health professionals of the second healthcare entity 1202 employing the first local information system 1204 and/or the second local information 1202.

In some examples, the cloud-based clinical information system 100 updates the patient records of the first clinical information system 1200 and/or the second clinical information system 1204 when information related to the patient is generated by other healthcare entities employing the cloud-based clinical information system 100. Thus, if the second healthcare entity 1204 subsequently refers the patient to a third healthcare entity, patient information (e.g., reports, images, and/or any other information) generated by the third healthcare entity may be automatically uploaded into the remote cloud system 302 and attached to the patient records of the first local information system 1204 and/or the second local information system 1206.

While an example manner of implementing the cloud-based clinical information system 100 of FIG. 1 is illustrated in FIGS. 3-5 and 12-14, one or more of the elements, processes and/or devices illustrated in FIGS. 3-5 and 12-14 may be combined, divided, re-arranged, omitted, eliminated and/or implemented in any other way. Further, the example architecture 300, the example remote cloud system 302, the example web/user interface tier 304, the example service tier 306, the example storage tier 308, the example edge device 310, the example local information systems 312, 314, the example notification services 316, the example event based services 318, 320, the example, application services 322, the example data services 324, the example identity management services 326, the example storage devices 328, 330, the example virtual machines 400, 402, 404, 406, 408, the example storage devices 410, 412, 414, 416, the example edge device 418, the example site 424, the example PACS 424, the example modalities 426, the example healthcare entities 500, the example internet 502, the example virtual machines 504, 506, 508, 510, 512, 514, 516, the example storage devices 518, 520, 522, the example first local information system 1204, the example second local information system 1206, the example second healthcare entity 1202, the example first healthcare entity 1200, the example edge device 1208, the example cloud application 1210, the records manager 1211, the example HL7 processor 1212, the example image storage devices 1214, the example healthcare information analytics engine 1216 and/or, more generally, the example cloud-based clinical information system 100 of FIG. 1 may be implemented by hardware, software, firmware and/or any combination of hardware, software and/or firmware. Thus, for example, any of the example architecture 300, the example remote cloud system 302, the example web/user interface tier 304, the example service tier 306, the example storage tier 308, the example edge device 310, the example local information systems 312, 314, the example notification services 316, the example event based services 318, 320, the example, application services 322, the example data services 324, the example identity management services 326, the example storage devices 328, 330, the example virtual machines 400, 402, 404, 406, 408, the example storage devices 410, 412, 414, 416, the example edge device 418, the example site 424, the example PACS 424, the example modalities 426, the example healthcare entities 500, the example internet 502, the example virtual machines 504, 506, 508, 510, 512, 514, 516, the example storage devices 518, 520, 522, the example first local information system 1204, the example second local information system 1206, the example second healthcare entity 1202, the example first healthcare entity 1200, the example edge device 1208, the example cloud application 1210, the records manager 1211, the example HL7 processor 1212, the example image storage devices 1214, the example healthcare information analytics engine 1216 and/or, more generally, the example cloud-based clinical information system 100 of FIG. 1 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example architecture 300, the example remote cloud system 302, the example web/user interface tier 304, the example service tier 306, the example storage tier 308, the example edge device 310, the example local information systems 312, 314, the example notification services 316, the example event based services 318, 320, the example, application services 322, the example data services 324, the example identity management services 326, the example storage devices 328, 330, the example virtual machines 400, 402, 404, 406, 408, the example storage devices 410, 412, 414, 416, the example edge device 418, the example site 424, the example PACS 424, the example modalities 426, the example healthcare entities 500, the example internet 502, the example virtual machines 504, 506, 508, 510, 512, 514, 516, the example storage devices 518, 520, 522, the example first local information system 1204, the example second local information system 1206, the example second healthcare entity 1202, the example first healthcare entity 1200, the example edge device 1208, the example cloud application 1210, the records manager 1211, the example HL7 processor 1212, the example image storage devices 1214, the example healthcare information analytics engine 1216 and/or, more generally, the example cloud-based clinical information system 100 of FIG. 1 is/are hereby expressly defined to include a tangible computer readable storage device or storage disk such as a memory, a digital versatile disk (DVD), a compact disk (CD), a Blu-ray disk, etc. storing the software and/or firmware. Further still, the example cloud-based clinical information system 100 may include one or more elements, processes and/or devices in addition to, or instead of, those illustrated in FIG. 1, and/or may include more than one of any or all of the illustrated elements, processes and devices.

Figure 15:
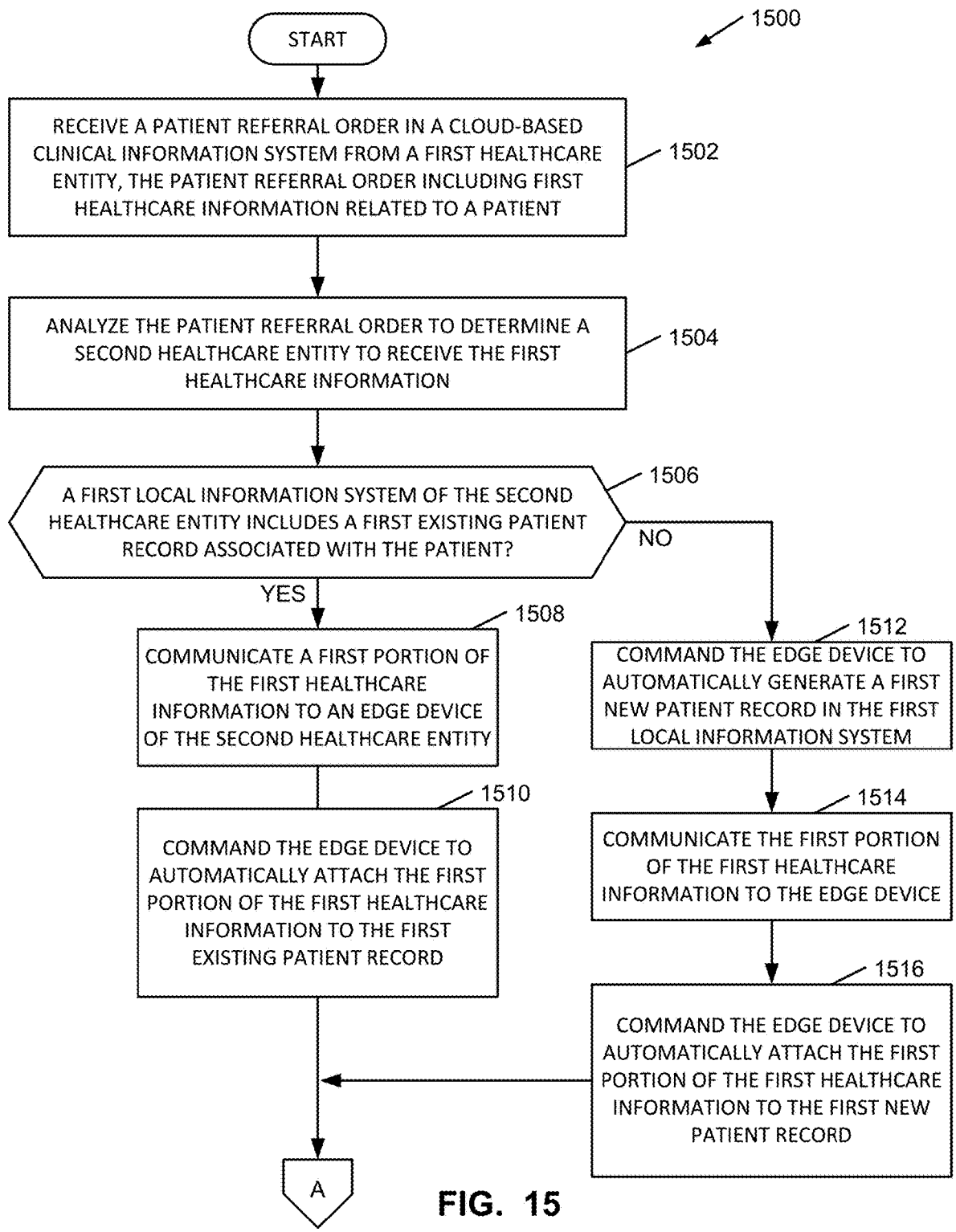
FIGS. 15-17 illustrate a flowchart representative of example machine-readable instructions which may be executed to automatically attach healthcare information stored in the cloud-based clinical information system of FIG. 12 to a patient record in the first local information system and/or the second local information system.
Figure 16:
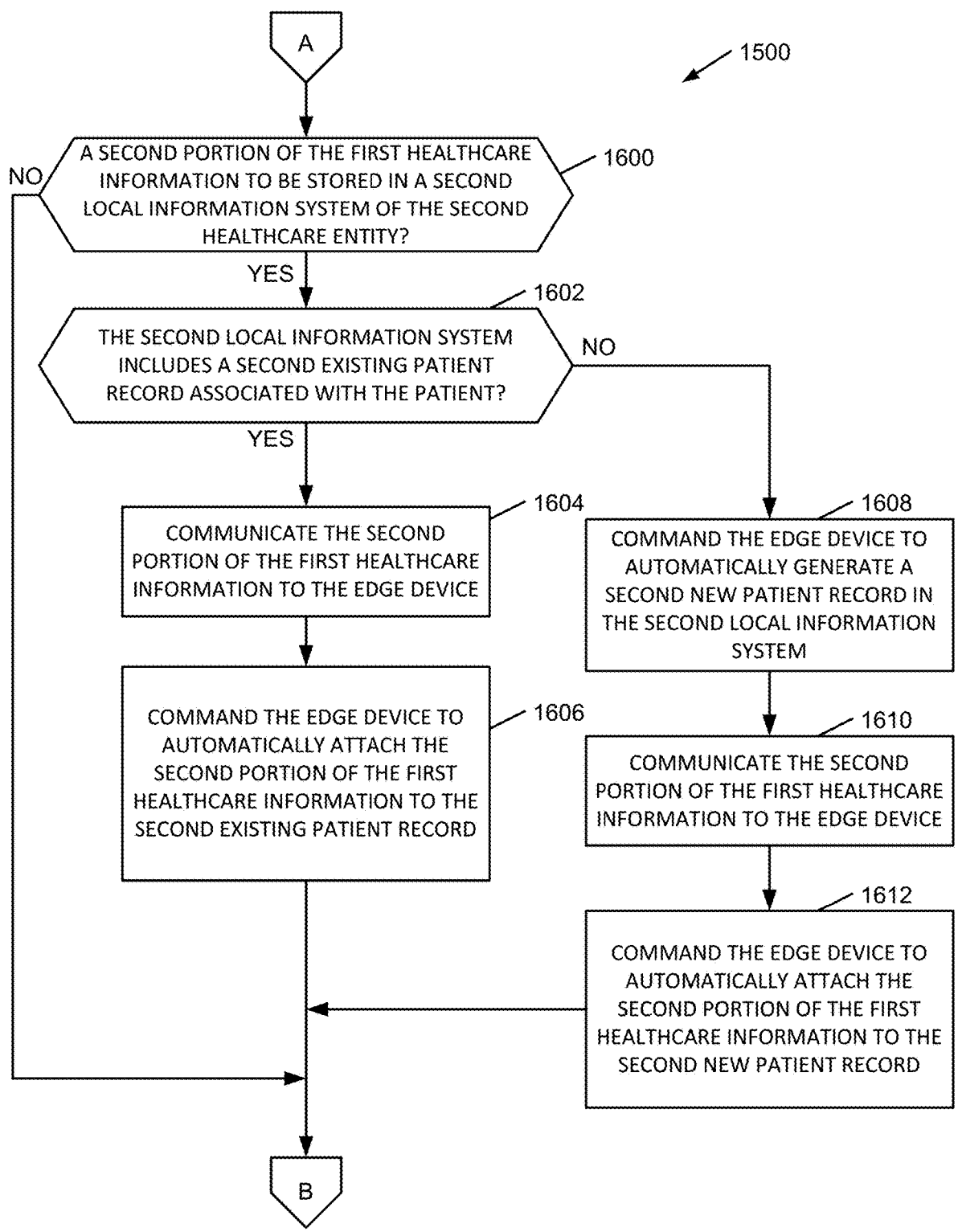
Figure 17:
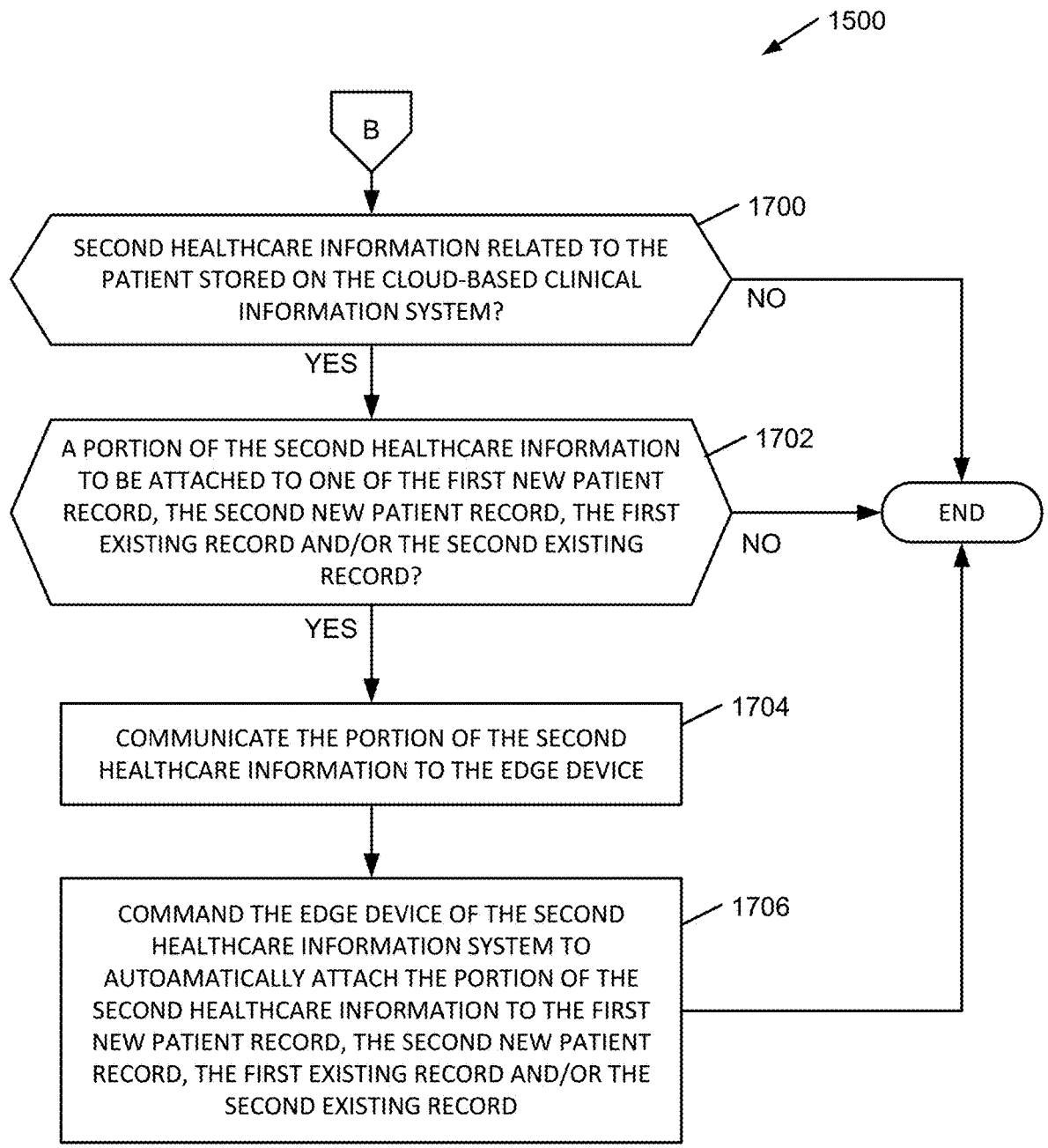

The example program 1500 of FIGS. 15-17 may be executed to integrate the cloud-based clinical information system 100 with one or more local information systems of a healthcare entity. For example, the program 1500 of FIGS. 15-17 may be executed to automatically attach healthcare information from the cloud-based clinical information system 100 to one or more medical records stored in the local information system(s) of the healthcare entity. In some examples, the program 1500 may be executed to automatically generate new patient records in the local information system(s) of the healthcare entity if the local information system(s) does not include an existing patient record and then automatically attach the healthcare information to the new patient records. Thus, when a first healthcare entity refers a patient to a second healthcare entity via the cloud-based clinical information system 100, the first healthcare entity may upload healthcare information onto the cloud-based clinical information system 100, and the cloud-based clinical information system 100 automatically stores the healthcare information onto the local information system(s) of the second healthcare entity.

The program 1500 of FIGS. 15-17 begins when the example healthcare information analytics engine 1216 of FIG. 12 receives a patient referral order in the cloud-based clinical information system 100 from the first healthcare entity 1200 (block 1502). In some examples, the patient referral order is uploaded onto and/or received by the cloud-based clinical information system 100 via a web-based application employing a public network such as the internet. In some examples, the patient referral order includes first healthcare information related to a patient. The first healthcare information may include, for example, one or more medical images (e.g., an x-ray image, an MRI image, etc.), medical reports, contact and/or demographic information of the patient and/or any other information related to the patient.

The example healthcare information analytics engine 1216 analyzes the patient referral order to determine that the second healthcare entity 1202 is to receive the first healthcare information to, for example, treat the patient based on the patient referral order (block 1504). In some examples, the cloud application 1210 communicates a notification to the second healthcare entity 1202 via the edge device 1208 located at a facility associated with the second healthcare entity 1202. For example, the notification services 324 may generate and communicate (e.g., via email, text message and/or any other way) notifications to a user of the example cloud-based clinical information system 100 associated with the second healthcare entity 1202. For example, if the patient referral order specifies a clinician employed by the second healthcare entity 1202 to treat the patient, the notification services 324 may generate and communicate a text message to a phone associated with the clinician. In some examples, the notification includes a link accessible via a web browser or a web application that enables the user to view the patient referral order and accept or decline the referral. In some examples, if the cloud-based clinical information system 100 receives an acceptance from the second healthcare entity, the instructions continue at block 1516.

The example healthcare information analytics engine 1216 determines if the first local information system 1204 includes a first existing patient record associated with the patient (block 1506). For example, the cloud-based clinical information system 100 may query the first local information system 1204 via the edge device 1208 to determine if the first local information system 1204 includes the first existing patient record. If the first local information system 1204 includes the first existing patient record, the records manager 1211 communicates a first portion of the first healthcare information to the edge device 1208 of the second healthcare entity 1202 (block 1508). In some examples, the records manager 1211 communicates the first portion of the first healthcare information by retrieving the first portion of the first healthcare information from the document and image storage device 1214 and sending the first portion of the first healthcare information to the edge device 1208 via, for example, a Secure DICOM data transmission. The records manager 1211 commands the edge device 1208 to automatically attach the first portion of the first healthcare information to the first existing patient record (block 1510). Thus, the first existing patient record may be automatically updated with the first portion of the first healthcare information.

In some examples, the healthcare information analytics engine 1216 determines if and/or which portion(s) of the first healthcare information such as a medical image is to be communicated to the edge device 1208 and/or attached to the first existing patient record based on one or more types of information employed by the first local information system 1204. For example, if the first local information system 1204 is a PACS, the healthcare information analytics engine 1216 may determine that medical images and information relating to the medical images in the first healthcare information is to be communicated to the edge device 1208 to be attached to the existing patient record in the first local information system 1204.

If the first local information system 1204 does not include the first existing patient record associated with the patient (block 1506), the records manager 1211 commands the edge device 1208 to automatically generate a first new patient record in the first local information system 1204 (block 1512). The example records manager 1211 communicates the first portion of the first healthcare information to the edge device 1208 (block 1514) and commands the edge device 1208 to automatically attach the first portion of the first healthcare information to the first new patient record. The example edge device 1208 then generates the first new patient record and attaches the first portion of the first healthcare information to the first new patient record.

In the illustrated example, the instructions 1500 continue when the healthcare information analytics engine 1216 determines if a second portion of the first healthcare information is to be stored in the second local information system 1206 of the second healthcare entity 1202. For example, if the second local information system 1206 is a radiology information system (RIS) and/or an electronic medical records (EMR) system, the healthcare information analytics engine 1216 determines if any portions of the first healthcare information include information that is to be stored in an MS or an EMR system. In some examples, the first local information system 1204 and the second local information system 1206 employ different secure protocols such as a DICOM protocol and an HL7 protocol, respectively. If the second portion of the first healthcare information is to be stored in the second local information system 1206, the example healthcare information analytics engine 1216 determines if the second local information system 1206 of the second healthcare entity 1202 includes a second existing patient record associated with the patient (block 1602). If the second local information system 1206 includes the second existing patient record, the records manager 1211 communicates the second portion of the first healthcare information to the edge device 1208 (block 1604) and commands the edge device 1208 to automatically attach the second portion of the first healthcare information to the second existing patient record (block 1606).

If the second local information system 1206 determines that the second local information system does not include the second existing patient record associated with the patient (block 1602), the records manager 1211 commands the edge device 1208 to automatically generate a second new patient record in the second local information system 1206 (block 1608), communicates the second portion of the first healthcare information to the edge device (block 1610), and commands the edge device 1208 to automatically attach the second portion of the first healthcare information to the second new patient record (block 1612). The example edge device 1208 then communicates with the example second local information system 1206 to automatically generate the second new patient record, and the edge device 1208 attaches the second portion of the first healthcare information to the second new patient record.

Once the records manager 1211 commands the edge device 1208 to automatically attach the second portion of the first healthcare information to the second existing patient record (block 1606) or the second new patient record (block 1612), or if the second portion of the first healthcare information is not to be stored in the second local information system 1206 (block 1600), the example instructions 1600 continue at block 1700 of FIG. 17. The healthcare information analytics engine 1216 determines if second healthcare information related to the patient is stored on the cloud-based clinical information system 100 (block 1700). For example, the patient may have been treated by one or more other healthcare entities employing the example cloud-based clinical information system 100, and the one or more other healthcare entities may have uploaded the second healthcare information onto the cloud-based clinical information system 100. In some examples, the healthcare information analytics engine 1216 monitors healthcare information uploaded onto the cloud-based clinical information system 100 by the one or more other healthcare entities and determines if the healthcare information is related to the patient via, for example, fuzzy logic.

If the second healthcare information is not stored on the cloud-based clinical information system 100, the example instructions 1500 end. If the second healthcare information is stored on the cloud-based clinical information system 100, the healthcare information analytics engine 1216 determines if a portion of the second healthcare information is to be attached to one or more of the first new patient record, the second new patient record, the first existing patient record, and/or the second existing patient record (block 1702). In some examples, the healthcare information analytics engine 1612 determines if the second healthcare information is to be attached to the first new patient record, the second new patient record, the first existing patient record, and/or the second existing patient record based on a request from the edge device 1208 for additional information related to the patient. For example, the edge device 1208 may communicates a request such as an HL7 order for the second healthcare information (e.g., additional healthcare information) related to the patient, and the healthcare information analytics engine 1216 collects HL7 order transactions that include the second healthcare information from the cloud-based clinical information system 100 and/or collects HL7 order transactions from local information systems of the one or more other healthcare entities. Based on the information collected and the local information systems 1204, 1206 employed by the second healthcare entity 1202, the healthcare information analytics engine 1216 determines if a portion of the second healthcare information is to be attached to the first new patient record, the second new patient record, the first existing patient record, and/or the second existing patient record. In some examples, the healthcare information analytics engine 1216 determines if the portion of the second healthcare information is to be attached to the first new patient record, the second new patient record, the first existing patient record, and/or the second existing patient record by querying the first local information system 1204 and/or the second local information system 1206.

If the portion of the second healthcare information is not to be attached to the first new patient record, the second new patient record, the first existing patient record, and/or the second existing patient record, the example instructions 1500 end. If the portion of the second healthcare information is to be attached to the first new patient record, the second new patient record, the first existing patient record, and/or the second existing patient record, the records manager 1211 communicates the portion of the second healthcare information to the edge device 1208 (block 1704) and commands the edge device 1208 to automatically attach the portion of the second healthcare information to the first new patient record, the second new patient record, the first existing patient record, and/or the second existing patient record. Thus, the example cloud-based clinical information system 100 may be used to collect and store a comprehensive and/or cohesive collection of healthcare information related to the patient.

Figure 18:
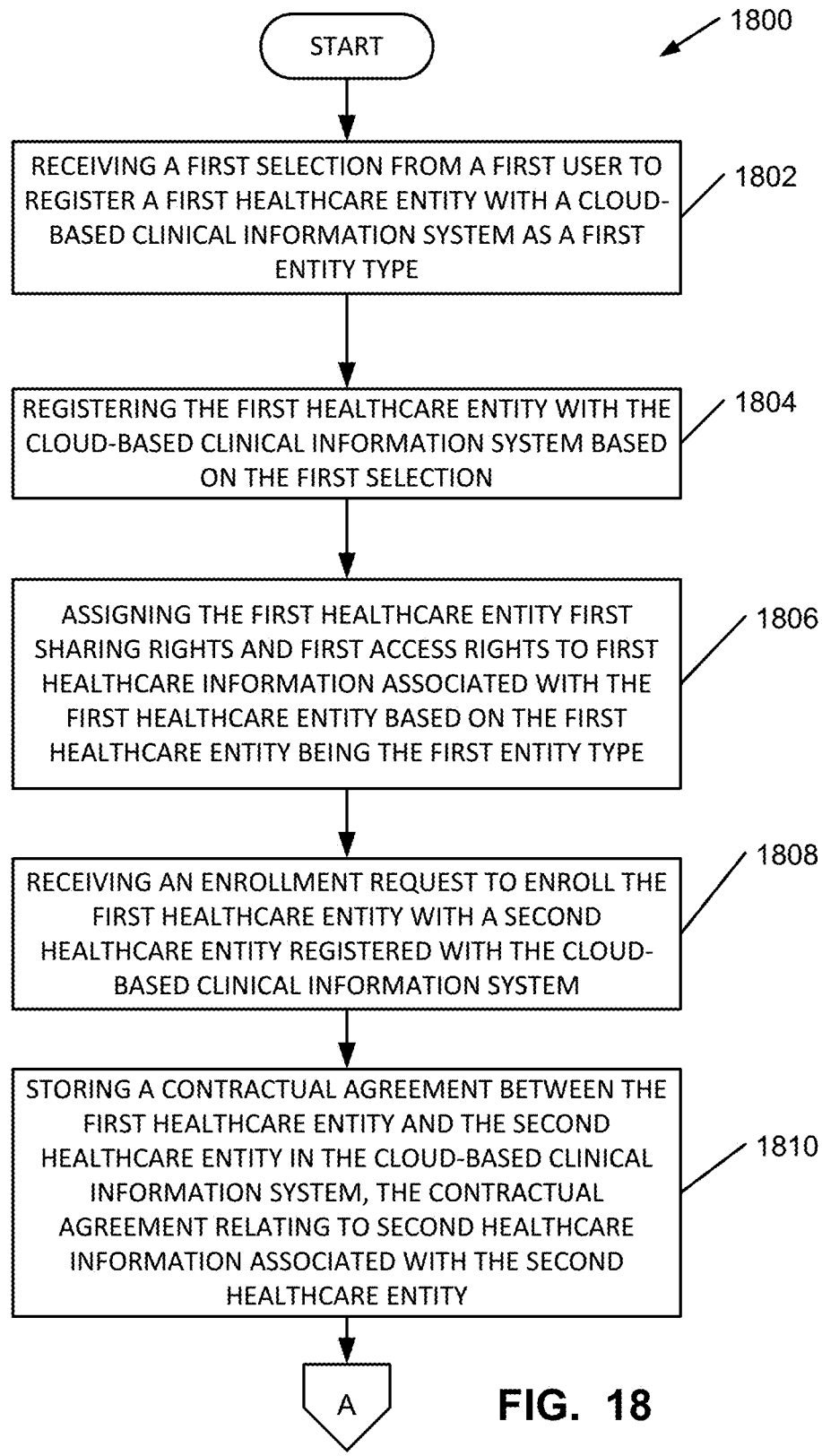
FIGS. 18-20 illustrate a flowchart representative of example machine-readable instructions which may be executed to register a first healthcare entity with the cloud-based clinical information system of FIG. 3 and enroll the first healthcare entity with a second healthcare entity registered with the example cloud-based clinical information system.
Figure 19:
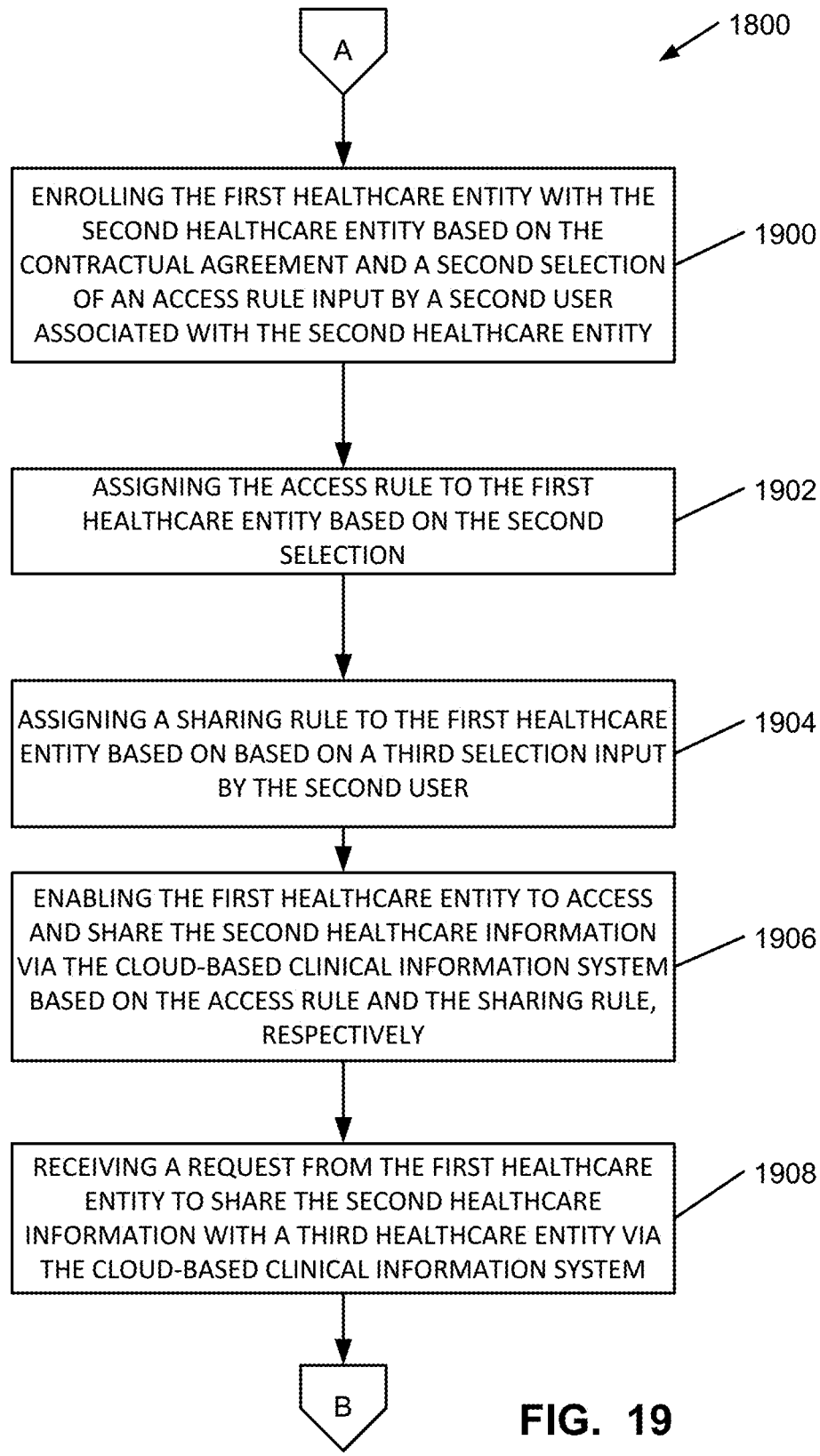
Figure 20:
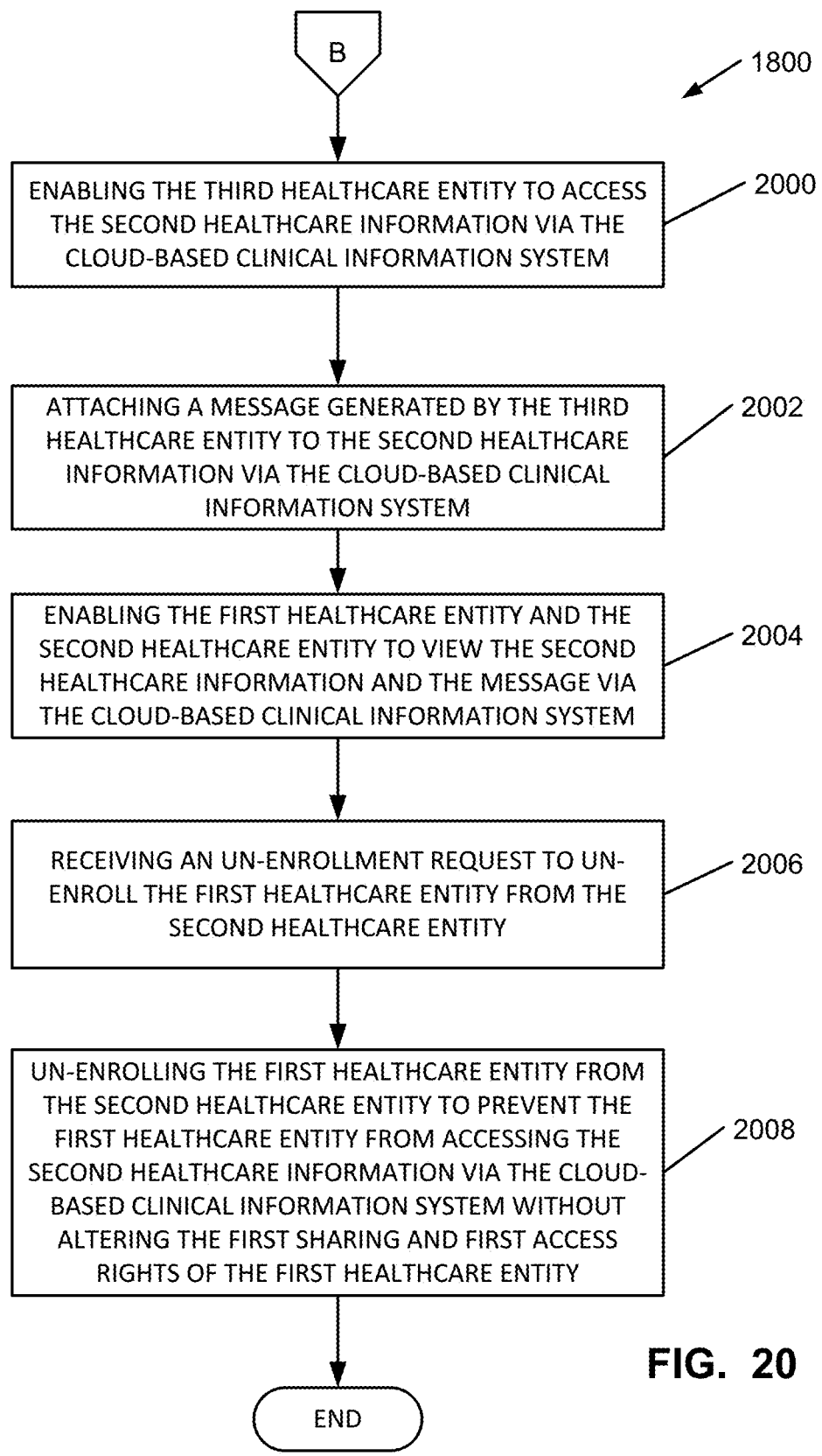

The example instructions 1800 of FIGS. 18-20 may be executed to enable healthcare entities to employ the cloud-based clinical information system 100, manage contractual agreements between the healthcare entities and enable the healthcare entities to collaborate with each other to treat patients. The example instructions 1800 of FIGS. 18-20 begin when the cloud-based clinical information system 100 receives a first selection from a first user to register a first healthcare entity with the cloud-based clinical information system 100 as a first entity type (block 1802). For example, the first user may employ a web browser or web-based application to input the first selection via a user interface generated by the user interface tier 304 of the example remote cloud system 302.

In some examples, the cloud-based clinical information system 100 enables the user to register the first healthcare entity as one of a plurality of entity types such as, for example, a patient, a clinician, a site, an integrated delivery network (IDN), a community and/or other entity types. In some examples, the entity types are organized hierarchically using, for example, the hierarchal organization scheme 200 of FIG. 2. In some examples, each of the entity types is associated with respective sharing and access rights to information uploaded onto the cloud-based clinical information system 100. For example, a healthcare entity registered as a patient may access information on the patient via the cloud-based clinical information system 100 from any healthcare entity employing the cloud-based clinical information system 100 and share the information on the patient with any healthcare entities via the cloud-based clinical information system 100. However, a healthcare entity registered as a clinician, for example, may only access healthcare information related to patients that the healthcare entity treated, is treating or is to treat. In some examples, a healthcare entity registered as a site may access healthcare information related to patients that have been or are under the care of the healthcare entity. For example, if the healthcare entity is a hospital registered as the site, a user associated with the hospital may access healthcare information related to patients treated in the hospital.

The cloud-based clinical information system 100 registers the first healthcare entity with the cloud-based clinical information 100 as the first entity type based on the first selection (block 1804). The example cloud-based clinical information system 100 assigns the first healthcare entity first sharing rights and first access rights to first healthcare information associated with the first healthcare entity based on the first healthcare entity being the first entity type (block 1806). In some examples, the first healthcare information is information that is uploaded onto the cloud-based clinical information system 100 by the first healthcare entity, information uploaded onto the cloud-based clinical information system 100 by other healthcare entities to share the information with the first healthcare entity and/or other information.

The cloud-based clinical information system 100 receives an enrollment request to enroll the first healthcare entity with a second healthcare entity registered with the cloud-based clinical information system 100 (block 1808). In some examples, the second healthcare entity is registered with the cloud-based clinical information system 100 as a second entity type the same as or different than the first entity type. In some examples, a contractual agreement related to the first healthcare information and/or second healthcare information associated with the second healthcare entity is uploaded onto the cloud-based clinical information system 100 by the first healthcare entity or the second healthcare entity. The second healthcare information may be, for example, information uploaded onto the cloud-based clinical information system 100 by the second healthcare entity, stored in one or more local information systems (e.g., PACS, an RIS/EMR system, etc.) of the second healthcare entity and/or other information. The cloud-based clinical information system 100 stores the contractual agreement between the first healthcare entity and the second healthcare entity in the cloud-based clinical information system 100 (block 1810).

The cloud-based clinical information system 100 enrolls the first healthcare entity with the second healthcare entity based on the contractual agreement and a second selection of an access rule input by a second user associated with the second healthcare entity (block 1900). For example, once the first healthcare entity requests enrollment (e.g., applies for membership) with the second healthcare entity, the cloud-based clinical information system 100 notifies the second healthcare entity. In some examples, the cloud-based clinical information system 100 queues an enrollment application of the first healthcare entity in a worklist of the second healthcare entity and sends an email to the second user (e.g., an administrator of the second healthcare entity) to notify the second user of the application. The second user may then review the application and approve and/or reject the application. In some examples, if the second user accepts the application, the second user may select the access rule that is to govern a scope of access of the first healthcare entity to the second healthcare information. For example, the access rule may enable the first healthcare entity to view the second healthcare information via a web browser of a workstation in communication with the cloud-based clinical information system but prevent the first healthcare entity from downloading the second healthcare information onto a local information system of the first healthcare entity. In some examples, the access rule enables the first healthcare entity to view and download the second healthcare information from the cloud-based clinical information system 100. In some examples, the access rule enables the first healthcare entity to access a local information system of the second healthcare entity via the cloud-based clinical information system to retrieve the second healthcare information. In other examples, the access rule governs the scope of the access of the first healthcare entity to the second healthcare information in other ways. Based on the second selection of the access rule, the cloud-based clinical information system 100 assigns the access rule to the first healthcare entity (block 1902).

In some examples, the second user inputs a third selection of a sharing rule for the first healthcare entity. In some examples, the sharing rule governs sharing of the second healthcare information via the cloud-based clinical information system 100 by the first healthcare entity. For example, the sharing rule may enable the first healthcare entity to share the second healthcare information with other healthcare entities specified by the second healthcare entity via the cloud-based clinical information system 100. In some examples, the sharing rule prevents the first healthcare entity from sharing the second healthcare information with other healthcare entities via the cloud-based clinical information system 100. The cloud-based clinical information system 100 assigns the sharing rule to the first healthcare entity based on the third selection (block 1904). In the illustrated example, the cloud-based clinical information system 100 enables the first healthcare entity to access and share the second healthcare information from the cloud-based clinical information system based on the access rule and the sharing rule, respectively (block 1906).

In the illustrated example, the cloud-based clinical information system 100 receives a request from the first healthcare entity to share the second healthcare information with a third healthcare entity via the cloud-based clinical information system 100 (block 1908). For example, the first healthcare entity may send the request to enable the third healthcare entity to access the second healthcare information to enable the first healthcare entity to collaborate with the third healthcare entity to treat a patient. For example, the first healthcare entity may send the request to enable the third healthcare entity to view the second healthcare information and provide a second opinion related to the patient. As discussed above, in some examples, an ability of the first healthcare entity to share the second healthcare information with the third healthcare entity is governed by the sharing rule selected by the second user associated with the second healthcare entity. In the illustrated example, the cloud-based clinical information system 100 enables the third healthcare entity to access the second healthcare information via the cloud-based clinical information system 100 (block 2000). In some examples, the third healthcare entity enrolls with the first healthcare entity to enable the third healthcare entity to access the second healthcare information shared by the first healthcare entity via the cloud-based clinical information system 100.

In the illustrated example, the third healthcare entity may view the second healthcare information via a web browser and/or a web-based application providing a user interface generated via the cloud-based clinical information system 100. In some examples, the third healthcare entity may generate information such as a message via the user interface and/or upload information (e.g., documents, medical images, etc.) to the cloud-based clinical information system 100 via the user interface. In the illustrated example, the cloud-based clinical information system 100 attaches a message generated by the third healthcare entity to the second healthcare information (block 2002). In some examples, attaching the message to the second healthcare information generates and/or updates a case history of a patient. The example cloud-based clinical information system 100 enables the first healthcare entity and the second healthcare entity to view the second healthcare information and the message via the cloud-based clinical information system (block 2004). Thus, the example first healthcare entity, the example second healthcare entity and the example third healthcare entity may collaborate to generate the case history to facilitate treatment of the patient.

In some examples, a business and/or contractual agreement between the first healthcare entity and the second healthcare entity may end or expire, and the second healthcare entity may send an un-enrollment request to the cloud-based clinical information system to prevent the first healthcare entity from subsequently accessing and sharing information associated with the second healthcare entity. The cloud-based clinical information system 100 receives the un-enrollment request to un-enroll the first healthcare entity from the second healthcare entity (block 2006) and un-enrolls the first healthcare entity from the second healthcare entity to prevent the first healthcare entity from accessing the second healthcare information via the cloud-based clinical information system 100 without altering the first sharing and first access rights of the first healthcare entity (block 2008). Thus, even after the first healthcare entity is un-enrolled with the second healthcare entity, the first healthcare entity may continue to employ the cloud-based clinical information system 100 to collaborate with other healthcare entities and access and share information associated with the first healthcare entity via the cloud-based clinical information system 100.

Figure 21:
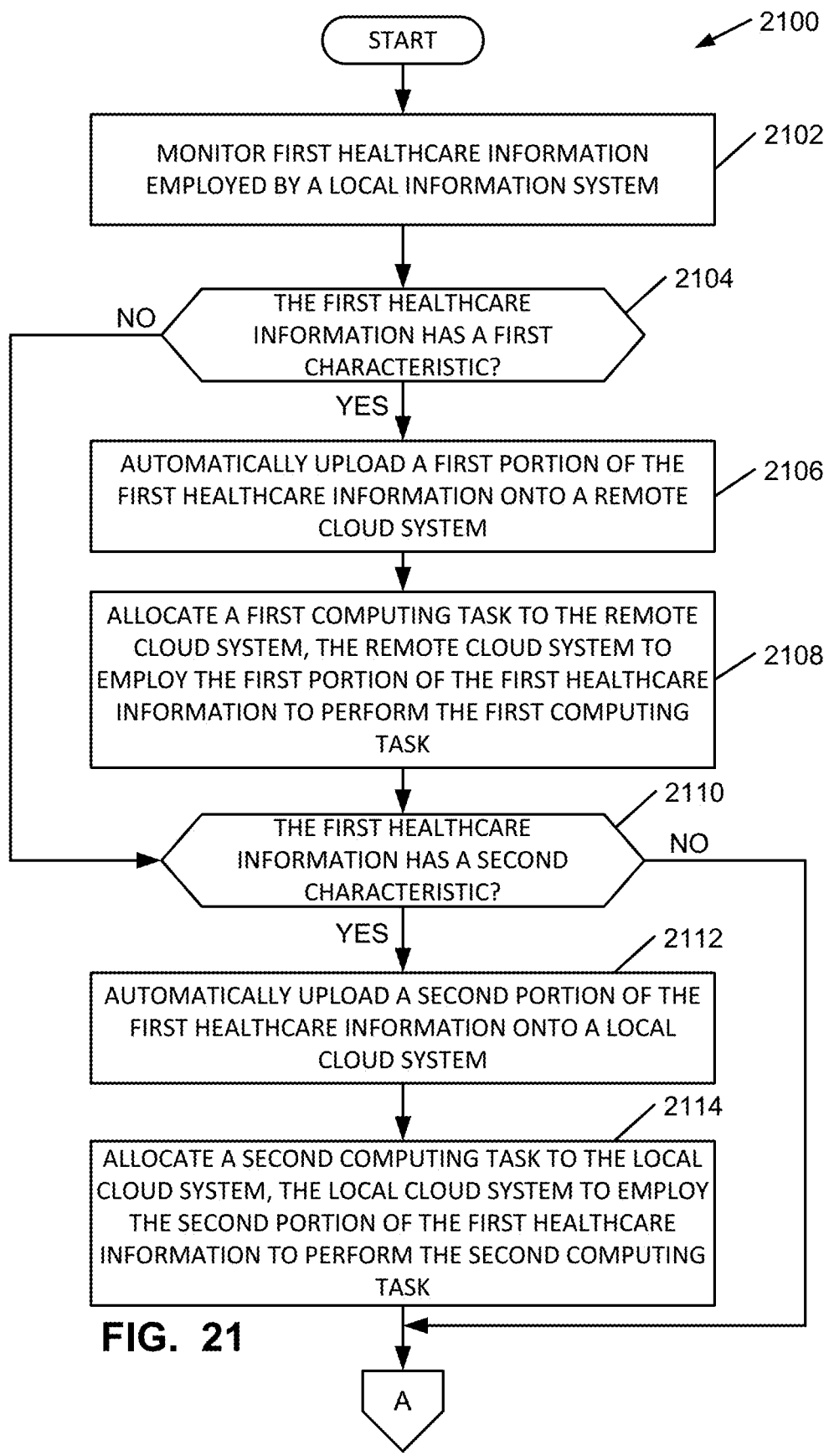
FIGS. 21-22 illustrate a flowchart representative of example machine-readable instructions which may be executed to implement an example hybrid cloud system disclosed herein.
Figure 22:
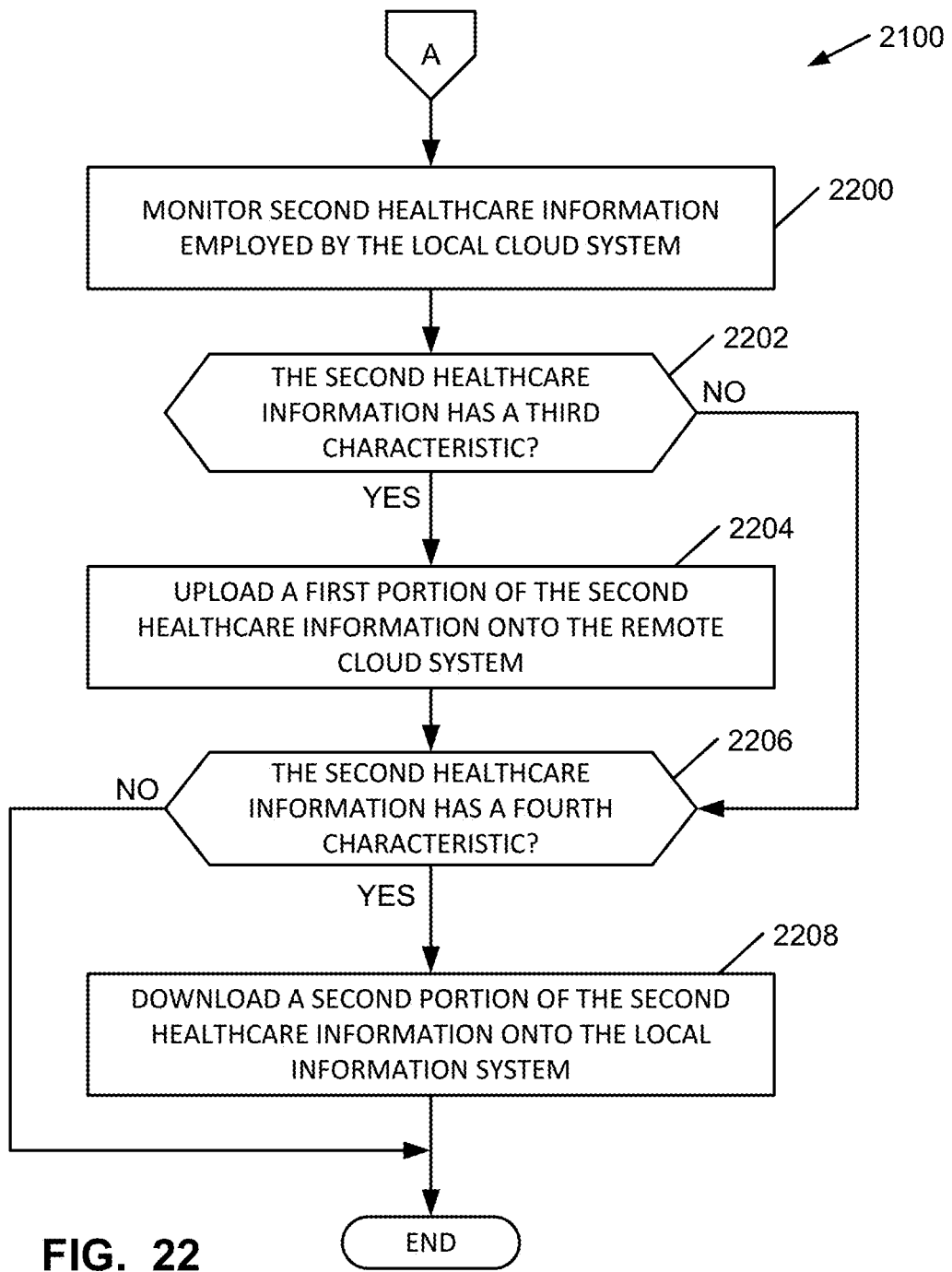

The example instructions 2100 of FIGS. 21-22 may be executed to implement an example hybrid cloud system that routs healthcare information and/or allocates computing tasks between, for example, the local information systems 312, 314, the local cloud system 342 and the remote cloud system 302 of FIG. 3. As described above in conjunction with FIG. 3, the remote cloud system 302 is accessible by a plurality of healthcare entities via a public network such as the internet. The healthcare entities may be unaffiliated with each other. For example, healthcare entities may be unaffiliated when no contractual or business agreements exist between the healthcare entities. The example local cloud system 342 of FIG. 3 is implemented by the example edge device 310. In some example, the local cloud system 342 is accessible only by the first healthcare entity 210 and a plurality of healthcare entities affiliated with the first healthcare entity via a private network such as a local area network (LAN) or a virtual private network (VPN). Healthcare entities may be affiliated when a contractual or business agreement or a legal relationship exists between the healthcare entities. For example, a second healthcare entity that is owned and/or operated by the first healthcare entity may be affiliated with the first healthcare entity.

The example instructions 2100 begin when the example edge device 310 monitors first healthcare information employed by the local information system 312 (block 2102). For example, the edge device 310 may periodically query the local information system 312 to determine if the first healthcare information has been uploaded onto the local information system 312. In some examples, the edge device 310 analyzes the first healthcare information by, for example, digesting parameters of the first healthcare information. The example edge device 310 determines if the first healthcare information has a first characteristic (block 2104). In some examples, the first characteristic is a computing task to be performed using the first healthcare information, a content of the first healthcare information, a storage destination of the first healthcare information, a source of the first healthcare information (e.g., an affiliated entity, an unaffiliated entity, etc.), an information type of the first healthcare information, a level of confidentiality associated with the first healthcare information, an clinical expertise associated with the first healthcare information, a type of clinical case associated with the first healthcare information, an association with a patient undergoing a medical procedure performed by a clinician associated with the first healthcare entity 210 and/or one or more other characteristics.

If the first healthcare information has the first characteristic, the example edge device 310 automatically uploads a first portion of the healthcare information onto the remote cloud system 302 (block 2106) and allocates a first computing task to the remote cloud system 302 (block 2108). The example remote cloud system 302 is to employ the first portion of the first healthcare information to perform the first computing task. The first computing task may be, for example, storing the first portion of the first healthcare information, enabling the first portion of the first healthcare information to be accessible to an unaffiliated healthcare entity via the remote cloud system 302 and/or other computing tasks.

In the illustrated example, the edge device 310 determines if the first healthcare information has a second characteristic (block 2110). In some examples, the second characteristic is a computing task to be performed using the first healthcare information, a content of the first healthcare information, a storage destination of the first healthcare information, a source of the first healthcare information, an information type of the first healthcare information, a level of confidentiality associated with the first healthcare information, an clinical expertise associated with the first healthcare information, a type of clinical case associated with the first healthcare information, an association with a patient undergoing a medical procedure performed by a clinician associated with the first healthcare entity 210 and/or one or more other characteristics. If the first healthcare information has the second characteristic, the example edge device 310 automatically uploads a second portion of the first healthcare information onto the local cloud system 342 (block 2112) and allocates a second computing task to the local cloud system 342 (block 2114). In some examples, the second portion of the first healthcare information includes the same information, different information and/or additional information relative to the first portion of the first healthcare information. In the illustrated example, the example local cloud system 342 is to employ the second portion of the first healthcare information to perform the second computing task. The second computing task may be, for example, storing the second portion of the first healthcare information, enabling the second portion of the first healthcare information to be accessible to an affiliated healthcare entity via the local cloud system 342 and/or other computing tasks.

In some examples in which the second characteristic is an association with a patient undergoing a medical procedure performed by a clinician associated the first healthcare entity 210, the clinician may be, for example, employed by one of the healthcare entities affiliated with the first healthcare entity 210. In some such examples, the edge device 310 uploads the second portion of the first healthcare information onto the local cloud system 342, and the local cloud system 342 stores the second portion of the first healthcare information while the patient undergoes the medical procedure. Thus, the second portion of the second healthcare information may be accessible to the one of the affiliated healthcare entities while the patient is undergoing the medical procedure. In some such examples, the edge device 310 removes the second portion of the healthcare information from the local cloud system 342 at a time after the medical procedure is performed. Thus, the local cloud system 342 may be used to temporarily store information related to a patient undergoing a medical procedure.

In the illustrated example, the edge device 310 also monitors second healthcare information employed by the local cloud system 342 (block 2200). For example, the edge device 310 may periodically query the local cloud system 342 for information uploaded onto the local cloud system 342 from one or more of the affiliated healthcare entities in communication with the local cloud system 342. In some examples, the edge device 310 monitors the second healthcare information employed by the local cloud system 342 by monitoring information communicated between affiliated healthcare entities via the local cloud system 342. In other examples, the edge device 310 monitors the second healthcare information in other ways. The example edge device 310 determines if the second healthcare information has a third characteristic (block 2202). The third characteristic may be, for example, a computing task to be performed using the second healthcare information, a content of the second healthcare information, a storage destination of the second healthcare information, a source of the second healthcare information, an information type of the second information, a level of confidentiality associated with the second healthcare information, an clinical expertise associated with the second healthcare information, a type of clinical case associated with the second healthcare information, an association with a patient undergoing a medical procedure performed by a clinician associated with the first healthcare entity 210 and/or one or more other characteristics. If the second healthcare information has the third characteristic, the example edge device 310 uploads a first portion of the second healthcare information onto the remote cloud system 302 (block 2204).

In the illustrated example, the edge device 310 also determines if the second healthcare information has a fourth characteristic (block 2206). The fourth characteristic may be, for example, a computing task to be performed using the second healthcare information, a content of the second healthcare information, a storage destination of the second healthcare information, a source of the second healthcare information, an information type of the second healthcare information, a level of confidentiality associated with the second healthcare information, an clinical expertise associated with the second healthcare information, a type of clinical case associated with the second healthcare information, an association with a patient undergoing a medical procedure performed by a clinician associated with the first healthcare entity 210 and/or one or more other characteristics. If the second healthcare information has the fourth characteristic, the edge device 310 downloads a second portion of the second healthcare information onto one or more of the first local information system 312 or the second local information system 314 (block 2208). In some examples, the second portion of the second healthcare information includes the same information, different information and/or additional information relative to the first portion of the second healthcare information. Thus, the edge device 310 may implement an example hybrid cloud system by allocating computing tasks and managing information flow between the local information systems 312, 314, the local cloud system 324, and the remote cloud system 302.

Figure 23:
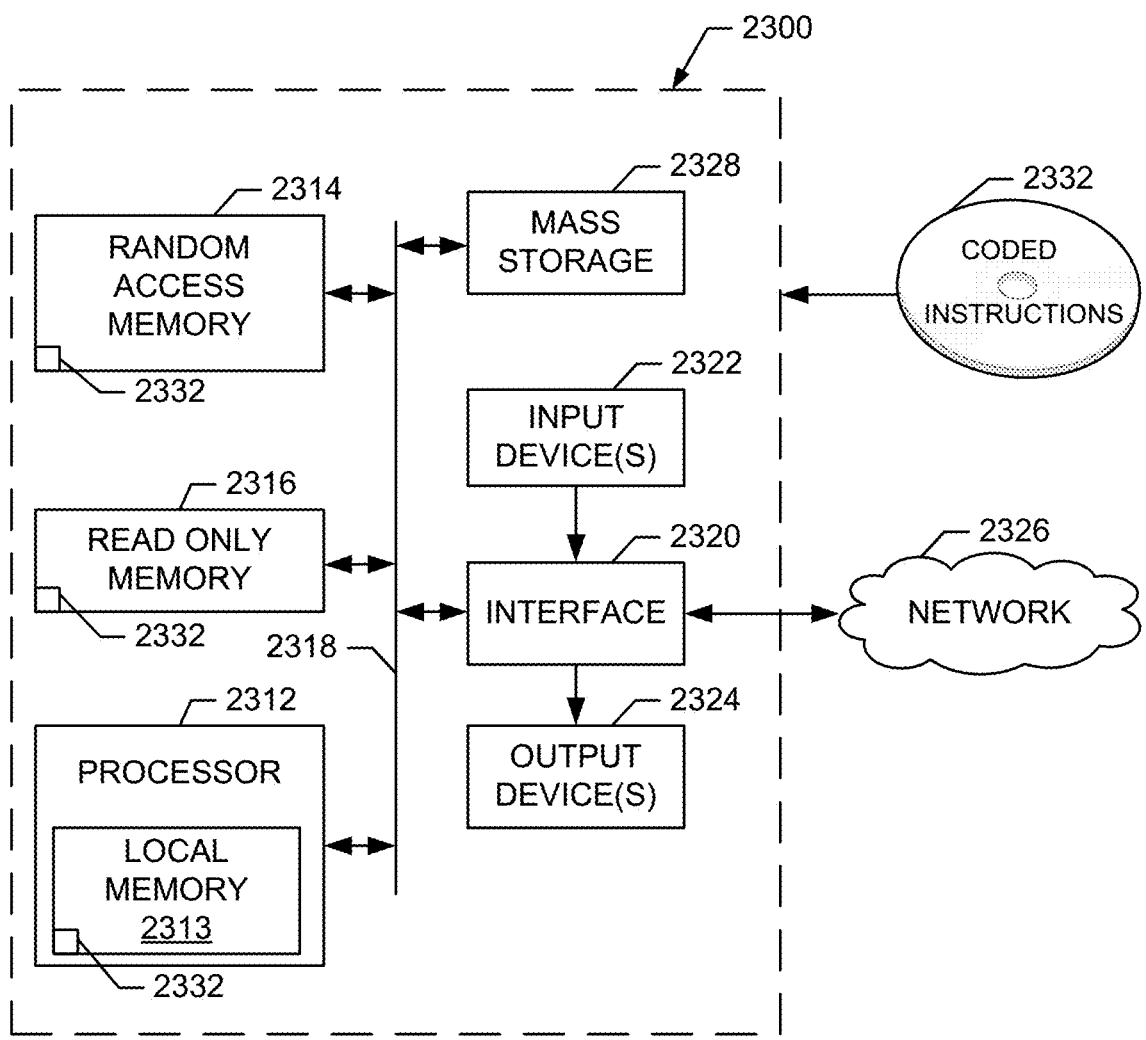
FIG. 23 is a block diagram of an example processor platform that may be used to implement the example systems and methods disclosed herein.

FIG. 23 is a block diagram of an example processor platform 2300 capable of executing the instructions of FIGS. 6-8 and 15-22 to implement the example clinical information system 100 of FIGS. 1, 3-5 and 12-14. The processor platform 2300 can be, for example, a server, a personal computer, a mobile device (e.g., a cell phone, a smart phone, a tablet such as an iPad™), a personal digital assistant (PDA), an Internet appliance, a DVD player, a CD player, a digital video recorder, a Blu-ray player, a gaming console, a personal video recorder, a set top box, or any other type of computing device.

The processor platform 2300 of the illustrated example includes a processor 2312. The processor 2312 of the illustrated example is hardware. For example, the processor 2312 can be implemented by one or more integrated circuits, logic circuits, microprocessors or controllers from any desired family or manufacturer.

The processor 2312 of the illustrated example includes a local memory 2313 (e.g., a cache). The processor 2312 of the illustrated example is in communication with a main memory including a volatile memory 2314 and a non-volatile memory 2316 via a bus 2318. The volatile memory 2314 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 2316 may be implemented by flash memory and/or any other desired type of memory device. Access to the main memory 2314, 2316 is controlled by a memory controller.

The processor platform 2300 of the illustrated example also includes an interface circuit 2320. The interface circuit 2320 may be implemented by any type of interface standard, such as an Ethernet interface, a universal serial bus (USB), and/or a PCI express interface.

In the illustrated example, one or more input devices 2322 are connected to the interface circuit 2320. The input device(s) 2322 permit(s) a user to enter data and commands into the processor 2312. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 2324 are also connected to the interface circuit 2320 of the illustrated example. The output devices 2324 can be implemented, for example, by display devices (e.g., a light emitting diode (LED), an organic light emitting diode (OLED), a liquid crystal display, a cathode ray tube display (CRT), a touchscreen, a tactile output device, a light emitting diode (LED), a printer and/or speakers). The interface circuit 2320 of the illustrated example, thus, typically includes a graphics driver card, a graphics driver chip or a graphics driver processor.

The interface circuit 2320 of the illustrated example also includes a communication device such as a transmitter, a receiver, a transceiver, a modem and/or network interface card to facilitate exchange of data with external machines (e.g., computing devices of any kind) via a network 2326 (e.g., an Ethernet connection, a digital subscriber line (DSL), a telephone line, coaxial cable, a cellular telephone system, etc.).

The processor platform 2300 of the illustrated example also includes one or more mass storage devices 2328 for storing software and/or data. Examples of such mass storage devices 2328 include floppy disk drives, hard drive disks, compact disk drives, Blu-ray disk drives, RAID systems, and digital versatile disk (DVD) drives.

The coded instructions 2332 of FIG. 23 may be stored in the mass storage device 2328, in the volatile memory 2314, in the non-volatile memory 2316, and/or on a removable tangible computer readable storage medium such as a CD or DVD.

The subject matter of this description may be implemented as stand-alone system or for execution as an application capable of execution by one or more computing devices. The application (e.g., webpage, downloadable applet or other mobile executable) can generate the various displays or graphic/visual representations described herein as graphic user interfaces (GUIs) or other visual illustrations, which may be generated as webpages or the like, in a manner to facilitate interfacing (receiving input/instructions, generating graphic illustrations) with users via the computing device(s).

Memory and processor as referred to herein can be stand-alone or integrally constructed as part of various programmable devices, including for example a desktop computer or laptop computer hard-drive, field-programmable gate arrays (FPGAs), application-specific integrated circuits (ASICs), application-specific standard products (ASSPs), system-on-a-chip systems (SOCs), programmable logic devices (PLDs), etc. or the like or as part of a Computing Device, and any combination thereof operable to execute the instructions associated with implementing the method of the subject matter described herein.

Computing device as referenced herein can include: a mobile telephone; a computer such as a desktop or laptop type; a Personal Digital Assistant (PDA) or mobile phone; a notebook, tablet or other mobile computing device; or the like and any combination thereof.

Computer readable storage medium or computer program product as referenced herein is tangible and can include volatile and non-volatile, removable and non-removable media for storage of electronic-formatted information such as computer readable program instructions or modules of instructions, data, etc. that may be stand-alone or as part of a computing device. Examples of computer readable storage medium or computer program products can include, but are not limited to, RAM, ROM, EEPROM, Flash memory, CD-ROM, DVD-ROM or other optical storage, magnetic cassettes, magnetic tape, magnetic disk storage or other magnetic storage devices, or any other medium which can be used to store the desired electronic format of information and which can be accessed by the processor or at least a portion of the computing device.

The terms module and component as referenced herein generally represent program code or instructions that causes specified tasks when executed on a processor. The program code can be stored in one or more computer readable mediums.

Network as referenced herein can include, but is not limited to, a wide area network (WAN); a local area network (LAN); the Internet; wired or wireless (e.g., optical, Bluetooth, radio frequency (RF)) network; a cloud-based computing infrastructure of computers, routers, servers, gateways, etc.; or any combination thereof associated therewith that allows the system or portion thereof to communicate with one or more computing devices.

The term user and/or the plural form of this term is used to generally refer to those persons capable of accessing, using, or benefiting from the present disclosure.

Technical effects of the subject matter described above can include, but is not limited to, providing cloud-based clinical information systems and associated methods. Moreover, the system and method of this subject matter described herein can be configured to provide an ability to better understand large volumes of data generated by devices across diverse locations, in a manner that allows such data to be more easily exchanged, sorted, analyzed, acted upon, and learned from to achieve more strategic decision-making, more value from technology spend, improved quality and compliance in delivery of services, better customer or business outcomes, and optimization of operational efficiencies in productivity, maintenance and management of assets (e.g., devices and personnel) within complex workflow environments that may involve resource constraints across diverse locations.

This written description uses examples to disclose the subject matter, and to enable one skilled in the art to make and use the invention. Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. A hybrid cloud system comprising:
   a cloud-based clinical information system including a first processor to generate a first user interface to enable a first user at a first local information system to interact with the cloud-based clinical information system and a second user interface to communicate with a second user employing the cloud-based clinical information system; and
   an edge device including a second processor to mediate information to be routed between the first local information system and the cloud-based clinical information system,
   wherein the edge device is to mediate by managing information traffic between the local information system and the cloud-based clinical information system generated by input via the first user interface, and wherein, when the first user and the second user are affiliated by a review board, the edge device is to manage information traffic related to a patient case to be examined in the review board between the first user and the second user and between the first and second users and the first local information system via the cloud-based clinical information system, the edge device triggered by the review board based on receipt of the patient case to determine a first affiliation of the first user and a second affiliation of the second user and compare the determined first and second affiliations to a third affiliation of the first local information system to manage information traffic to the review board by a) providing the information in a first form to at least one of the first user or the second user in the review board when the respective at least one of the first affiliation or the second affiliation matches the third affiliation and by b) providing the information in a second form to at least one of the first user or the second user in the review board when the respective at least one of the first affiliation or the second affiliation does not match the third affiliation, the cloud-based clinical information system to provide the first and second user interfaces to enable the first and second users to collaborate to conduct the review board in conjunction with content of the patient case managed and provided for viewing according to the first, second, and third affiliations via the edge device in the review board.

2. The system of claim 1, wherein the first local information system is to communicate using a first protocol and wherein the second user is to employ the cloud-based clinical information system via a second local information system that is to communicate using a second protocol, the edge device to mediate between the first protocol and the second protocol to exchange information between the first user interface and the second user interface.

3. The system of claim 1, wherein the review board is to enable collaboration between the first user and the second user via the first user interface and the second user interface regarding the patient case, the collaboration to include an exchange of information to be mediated by the edge device and generation of a report for treatment of the patient case.

4. The system of claim 1, wherein the edge device is to share information from a local cloud system to the first user interface and the second user interface when the first user and second user are affiliated.

5. The system of claim 1, wherein the review board includes a tumor review board.

6. The system of claim 1, wherein the edge device is to anonymize the patient case in the second form to be shared via a least one of the cloud-based clinical information system or a local cloud system when at least one of the first user or the second user is unaffiliated.

7. The system of claim 1, wherein the edge device and the first local information system are to be located at a first site and wherein the cloud-based clinical information system is to be located at a second site.

8. The system of claim 1, wherein the first local information system is to be accessible via a first network and the cloud-based clinical information system is to be accessible via a second network, and wherein the edge device is to mediate access between the first network and the second network.

9. The system of claim 8, wherein the first network includes a private network and wherein the second network includes a public network.

10. The system of claim 1, wherein the edge device is implemented using one or more virtual machines to identify the first and second users, match affiliation, and manage access to information for the patient case in the review board.

11. The system of claim 1, wherein the edge device interacts with a service tier and a user interface tier of a remote cloud system to provide the information for the patient case and facilitate the review board between the first user and the second user.

12. A non-transitory computer-readable storage medium including instructions that, when executed, cause at least one processor to implement at least:

a cloud-based clinical information system to generate a first user interface to enable a first user at a first local information system to interact with the cloud-based clinical information system and a second user interface to communicate with a second user employing the cloud-based clinical information system; and an edge device to mediate information to be routed between the first local information system and the cloud-based clinical information system, wherein the edge device is to mediate by managing information traffic between the local information system and the cloud-based clinical information system generated by input via the first user interface, and wherein, when the first user and the second user are affiliated by a review board, the edge device is to manage information traffic related to a patient case to be examined in the review board between the first user and the second user and between the first and second users and the first local information system via the cloud-based clinical information system, the edge device triggered by the review board based on receipt of the patient case to determine a first affiliation of the first user and a second affiliation of the second user and compare the determined first and second affiliations to a third affiliation of the first local information system to manage information traffic to the review board by a) providing the information in a first form to at least one of the first user or the second user in the review board when the respective at least one of the first affiliation or the second affiliation matches the third affiliation and by b) providing the information in a second form to at least one of the first user or the second user in the review board when the respective at least one of the first affiliation or the second affiliation does not match the third affiliation, the cloud-based clinical information system to provide the first and second user interfaces to enable the first and second users to collaborate to conduct the review board in conjunction with content of the patient case managed and provided for viewing according to the first, second, and third affiliations via the edge device in the review board.

13. The computer-readable storage medium of claim 12, wherein the instructions, when executed, cause the first local information system to communicate using a first protocol and wherein the second user is to employ the cloud-based clinical information system via a second local information system that is to communicate using a second protocol, the edge device to mediate between the first protocol and the second protocol to exchange information between the first user interface and the second user interface.

14. The computer-readable storage medium of claim 12, wherein the review board is to enable collaboration between the first user and the second user via the first user interface and the second user interface regarding the patient case, the collaboration to include an exchange of information to be mediated by the edge device and generation of a report for treatment of the patient case.

15. The computer-readable storage medium of claim 12, wherein instructions, when executed, cause the edge device to share information from a local cloud system to the first user interface and the second user interface when the first user and second user are affiliated.

16. The computer-readable storage medium of claim 12, wherein the review board includes a tumor review board.

17. The computer-readable storage medium of claim 12, wherein the instructions, when executed, cause the edge device to anonymize the patient case to be shared via a least one of the cloud-based clinical information system or a local cloud system.

18. The computer-readable storage medium of claim 12, wherein the edge device and the first local information system are to be located at a first site and wherein the cloud-based clinical information system is to be located at a second site.

19. The computer-readable storage medium of claim 12, wherein the first local information system is to be accessible via a first network and the cloud-based clinical information system is to be accessible via a second network, and wherein the edge device is to mediate access between the first network and the second network.

20. The computer-readable storage medium of claim 19, wherein the first network includes a private network and wherein the second network includes a public network.

21. A non-transitory computer-readable storage medium including instructions that, when executed, cause at least one processor to implement at least:
    enable interaction between a first user interface for a first user at a first local information system and a cloud-based clinical information system;
    enable interaction between the first user interface and a second user interface to communicate with a second user employing the cloud-based clinical information system;
    mediate information to be routed between the first local information system and the cloud-based clinical information system by managing information traffic between the local information system and the cloud-based clinical information system generated by input via the first user interface; and
    when the first user and the second user are affiliated by a review board, share information related to a patient case to be examined by the review board between the first user and the second user via the cloud-based clinical information system,
    wherein mediating information includes, when triggered by the review board based on receipt of the patient case, determining a first affiliation of the first user and a second affiliation of the second user and comparing the determined first and second affiliations to a third affiliation of the first local information system to manage information traffic to the review board by a) providing the information in a first form to at least one of the first user or the second user in the review board when the respective at least one of the first affiliation or the second affiliation matches the third affiliation and by b) providing the information in a second form to at least one of the first user or the second user in the review board when the respective at least one of the first affiliation or the second affiliation does not match the third affiliation, and
    wherein the first and second user interfaces are provided to enable the first and second users to collaborate to conduct the review board in conjunction with content of the patient case managed and provided for viewing according to the first, second, and third affiliations in the review board.

22. The computer-readable storage medium of claim 21, wherein the computer-readable storage medium is included in an edge device.

* * * * *